(12) United States Patent
Salcudean

(10) Patent No.: US 10,085,703 B2
(45) Date of Patent: Oct. 2, 2018

(54) DYNAMIC COMPUTED TOMOGRAPHY IMAGING OF ELASTICITY

(71) Applicant: Septimiu Edmund Salcudean, Vancouver (CA)

(72) Inventor: Septimiu Edmund Salcudean, Vancouver (CA)

(*) Notice: Subject to any disclaimer, the term of this patent is extended or adjusted under 35 U.S.C. 154(b) by 291 days.

(21) Appl. No.: 15/008,014

(22) Filed: Jan. 27, 2016

(65) Prior Publication Data

US 2016/0213341 A1    Jul. 28, 2016

Related U.S. Application Data

(60) Provisional application No. 62/108,326, filed on Jan. 27, 2015.

(51) Int. Cl.
    *A61B 6/03*    (2006.01)
    *A61B 6/00*    (2006.01)
    *A61B 5/00*    (2006.01)

(52) U.S. Cl.
    CPC .............. *A61B 6/50* (2013.01); *A61B 6/032* (2013.01); *A61B 6/503* (2013.01); *A61B 6/52* (2013.01); *A61B 6/5205* (2013.01); *A61B 6/5217* (2013.01); *A61B 5/0051* (2013.01)

(58) Field of Classification Search
    CPC ........... A61B 6/032; A61B 6/50; A61B 6/503; A61B 6/52; A61B 6/5205; A61B 6/5217
    USPC ....................................................... 378/4, 901
    See application file for complete search history.

(56) References Cited

U.S. PATENT DOCUMENTS

| | | | | |
|---|---|---|---|---|
| 6,522,712 B1* | 2/2003 | Yavuz | ................... | G06T 11/005 378/4 |
| 6,879,656 B2* | 4/2005 | Cesmeli | ................. | A61B 6/032 378/19 |
| 7,231,076 B2* | 6/2007 | Fu | ........................ | G06K 9/3233 378/4 |
| 7,315,605 B2* | 1/2008 | Boese | .................... | A61B 6/032 378/8 |
| 7,327,865 B2* | 2/2008 | Fu | ........................... | G06K 9/32 378/28 |

(Continued)

OTHER PUBLICATIONS

Liu et al, "Tomography-Based 3-D Anisotropic Elastography Using Boundary Measurements", IEEE Trans. On Medical Imaging, vol. 24, No. 10, Oct. 2005.

(Continued)

*Primary Examiner* — Allen C. Ho
(74) *Attorney, Agent, or Firm* — Borden Ladner Gervais LLP; Todd A. Keeler

(57) ABSTRACT

A system and method includes applying, by a vibration source, periodic excitation waves to the volume of tissue, the periodic excitation wave having a plurality of phases, acquiring by the CT scanner a first plurality of CT projections at a first phase, the first plurality of CT projections comprising a first CT projection set, acquiring by the CT scanner a second plurality of CT projections at a second phase, wherein the second phase is different than the first phase a second set of CT projections, the second plurality of CT projections comprising a second CT projection set, and determining, based on the first set of CT projections and the second set of CT projections, at least one of a tissue deformation field and a tissue mechanical property of the volume of tissue.

19 Claims, 11 Drawing Sheets

(56) References Cited

U.S. PATENT DOCUMENTS

| | | | | |
|---|---|---|---|---|
| 7,330,578 | B2* | 2/2008 | Wang | G06T 15/08 |
| | | | | 345/419 |
| 7,366,278 | B2* | 4/2008 | Fu | G06T 11/008 |
| | | | | 345/419 |
| 7,415,093 | B2* | 8/2008 | Tkaczyk | A61B 6/541 |
| | | | | 378/4 |
| 7,426,318 | B2* | 9/2008 | Fu | G06T 7/344 |
| | | | | 382/294 |
| 7,443,946 | B2* | 10/2008 | Deller | A61B 6/541 |
| | | | | 378/8 |
| 7,477,771 | B2* | 1/2009 | Iatrou | A61B 6/032 |
| | | | | 378/4 |
| 7,505,037 | B2* | 3/2009 | Wang | G06T 7/00 |
| | | | | 345/424 |
| 7,522,779 | B2* | 4/2009 | Fu | A61B 6/5235 |
| | | | | 278/54 |
| 7,599,540 | B2* | 10/2009 | Koehler | G06T 11/006 |
| | | | | 378/21 |
| 7,630,528 | B2* | 12/2009 | Kohler | G06T 11/006 |
| | | | | 378/4 |
| 7,782,998 | B2* | 8/2010 | Langan | G01N 23/046 |
| | | | | 378/8 |
| 7,899,152 | B2* | 3/2011 | Boese | A61B 6/025 |
| | | | | 378/8 |
| 8,135,196 | B2* | 3/2012 | Heigl | A61B 6/032 |
| | | | | 378/98.12 |
| 8,175,359 | B2* | 5/2012 | O'Halloran | G01R 33/4824 |
| | | | | 382/131 |
| 8,184,886 | B2* | 5/2012 | Khamene | A61B 6/5235 |
| | | | | 382/131 |
| 8,194,937 | B2* | 6/2012 | Chen | G06T 11/006 |
| | | | | 382/131 |
| 8,229,187 | B2* | 7/2012 | Deller | A61B 5/113 |
| | | | | 382/128 |
| 8,229,199 | B2* | 7/2012 | Chen | G06T 11/006 |
| | | | | 382/128 |
| 8,275,448 | B2* | 9/2012 | Camus | A61B 6/12 |
| | | | | 600/428 |
| 8,295,912 | B2* | 10/2012 | Gertner | A61B 8/06 |
| | | | | 600/424 |
| 8,374,413 | B2* | 2/2013 | Chen | G06T 11/006 |
| | | | | 378/901 |
| 8,394,026 | B2 | 3/2013 | Eskandari et al. | |
| 8,472,688 | B2* | 6/2013 | Samsonov | G01R 33/4818 |
| | | | | 382/130 |
| 8,483,463 | B2* | 7/2013 | Chen | G06T 11/006 |
| | | | | 382/131 |
| 8,538,111 | B2* | 9/2013 | Zhang | A61B 5/08 |
| | | | | 382/131 |
| 8,548,568 | B2* | 10/2013 | Hsieh | A61B 6/5264 |
| | | | | 600/427 |
| 8,705,827 | B2* | 4/2014 | Zhu | G06T 5/002 |
| | | | | 378/7 |
| 8,824,756 | B2* | 9/2014 | Joshi | G06T 11/006 |
| | | | | 382/128 |
| 8,874,187 | B2* | 10/2014 | Thomson | A61B 6/037 |
| | | | | 378/62 |
| 8,897,514 | B2* | 11/2014 | Feikas | G06T 7/20 |
| | | | | 382/128 |
| 9,013,471 | B2* | 4/2015 | Lauritsch | A61B 6/504 |
| | | | | 345/419 |
| 9,031,300 | B1* | 5/2015 | Manjeshwar | G06T 11/003 |
| | | | | 382/128 |
| 9,047,701 | B2* | 6/2015 | Brehm | A61B 6/5235 |
| 9,092,666 | B2* | 7/2015 | Kang | G06K 9/00362 |
| 9,129,426 | B2* | 9/2015 | Gopalakrishnan | G06T 11/005 |
| 9,129,431 | B2* | 9/2015 | Maeda | A61B 6/032 |
| 9,366,738 | B2* | 6/2016 | Chase | G01R 33/4818 |
| 9,489,736 | B2* | 11/2016 | Lodron | G06T 7/0024 |
| 9,495,746 | B2* | 11/2016 | Chou | G06T 7/0034 |
| 9,514,550 | B2* | 12/2016 | Taguchi | A61B 6/5264 |
| 9,684,980 | B2* | 6/2017 | Royalty | G06T 11/003 |
| 9,801,615 | B2* | 10/2017 | Salcudean | A61B 8/485 |
| 2014/0330122 | A1 | 11/2014 | Baghani et al. | |

OTHER PUBLICATIONS

Ehrhardt, et al., An optical flow based method for improved reconstruction of 4D CT data sets acquired during free breathing, Med. Phys. 34 (2) (2007) 711-721.

Pan et al., 4D-CT imaging of a volume influenced by respiratory motion on multi-slice CT, Med. Phys. 31 (2), (2004) 333-340.

Wang et al., A knowledge-based cone-beam X-ray CT algorithm for dynamic volumetric cardiac imaging, Med. Phys. 29 (8) (2002) 1807-1822.

Paul et al., "Strategies for reduction of radiation does in cardiac multislice CT", Eur. Radiol., 2007, 17:2028-2037.

Keall et al. The management of respiratory motion in radiation oncology report of AAPM Task Group 76. Med Phys 2006; 33:3874-900.

Kudo et al. "Image reconstruction for sparse-view CT and interior-CT—introduction to compressed sensing and differentiated backprojection" (2013), Quantitative Imaging in Medicine and Surgery, 3(3), pp. 147-161.

Zahiri et al., "Sub-sample displacement estimation from digitized ultrasound RF signals using multi-dimensional polynomial fitting of the cross-correlation function." Ultrasonics, Ferroelectrics and Frequency Control, IEEE Transactions on 57.11 (2010): 2403-2420.

Heinrich et al., (2012). MIND: Modality independent neighbourhood descriptor for multi-modal deformable registration. Medical Image Analysis, 16(7), 1423-1435.

Salcudean et al., "Viscoelasticity modeling of the prostate region using vibro-elastography." Medical Image Computing and Computer-Assisted Intervention—MICCAI 2006. Springer Berlin Heidelberg, 2006. 389-396.

Eskandari et al.,(2008), "Viscoelastic parameter estimation based on spectral analysis", IEEE Transactions on Ultrasonics, Ferroelectrics and Frequency Control, 55(7), 1611-1625.

Moradi et al. (2014). Multiparametric 3D in vivo ultrasound vibroelastography imaging of prostate cancer: Preliminary results. Medical physics, 41(7), 073505.

Eskandari et al.,(2008), "Viscoelastic characterization of soft tissue from dynamic finite element models", Physics in medicine and biology, 53(22), 6569.

Honarvar et al., (Mar. 2014) "Vibro-elastoraphy: Direct FEM inversion of the shear wave equation without the local homogeneity assumption", Medical Imaging 2014: Ultrasonic Imaging and Tomography, Proc. of SPIE vol. 9040, 904003-1.

Honarvar et al., (2013). Curl-based Finite Element Reconstruction of the Shear Modulus Without Assuming Local Homogeneity: Time Harmonic Case, IEEE Transactions on Medical Imaging, vol. 32, No. 12, Dec. 2013, 0278-0062.

Honarvar et al., "Sparsity regularization in dynamic elastography." Physics in medicine and biology 57, No. 19 (2012): 5909-5927.

Saremi, F., "Congenital Pericardial Anomalies", Cardiac CT and MR for Adult Congenital Heart Disease, Doi 10.1007/978-1-4614-8875-0_29 (2014).

Candés et al., "Enhancing sparsity by reweighted l1 Minimization", (2008) J Fourier Anal Appl (2008) 14:877-905; DOI 10.1007/s00041-008-9045-x.

* cited by examiner

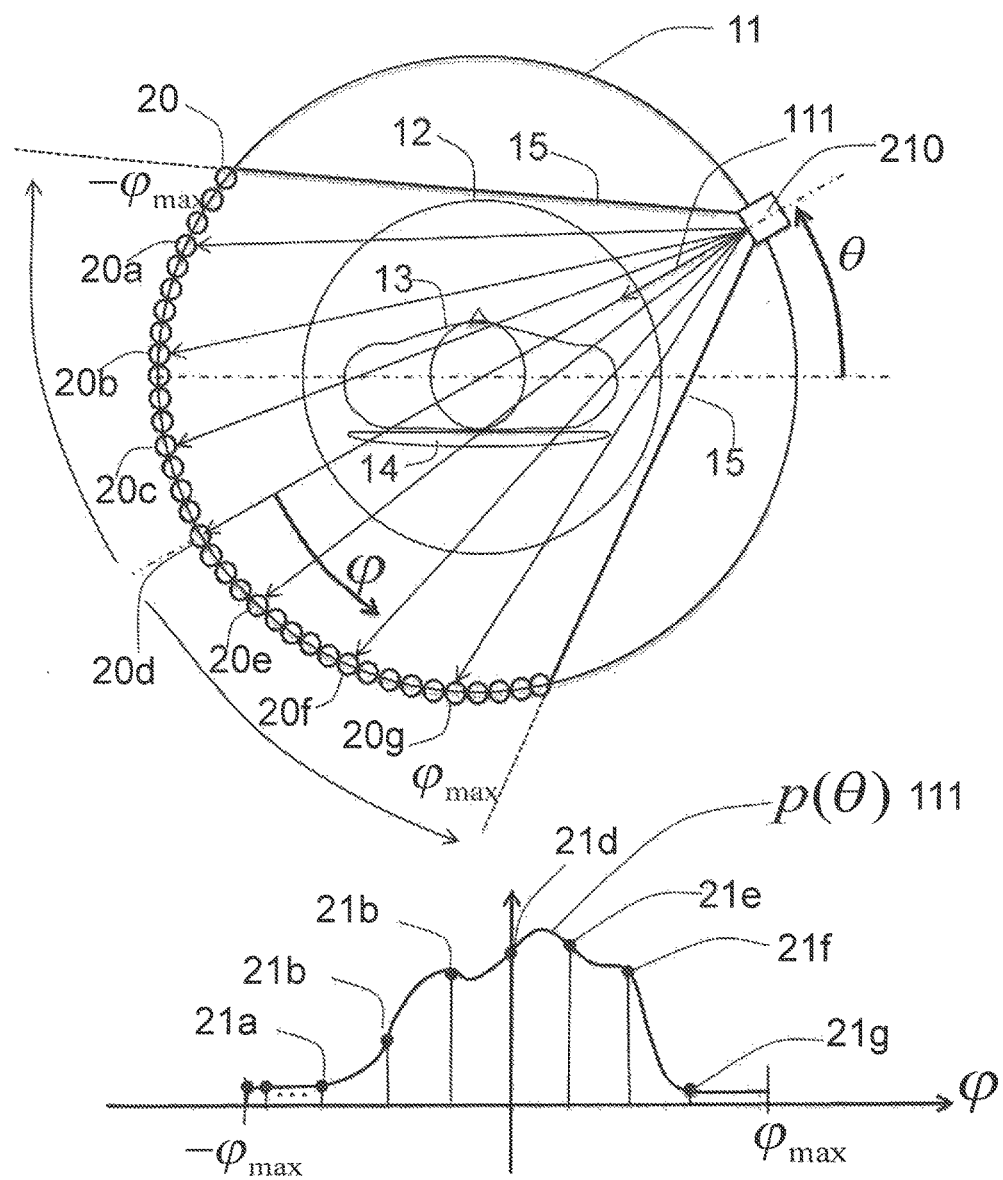

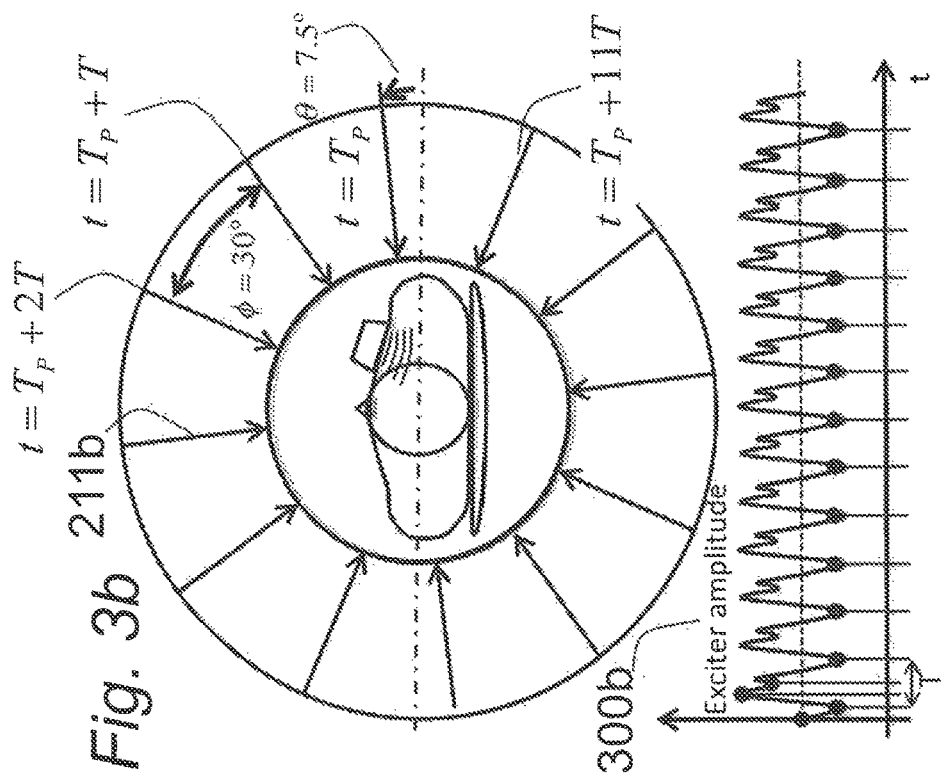
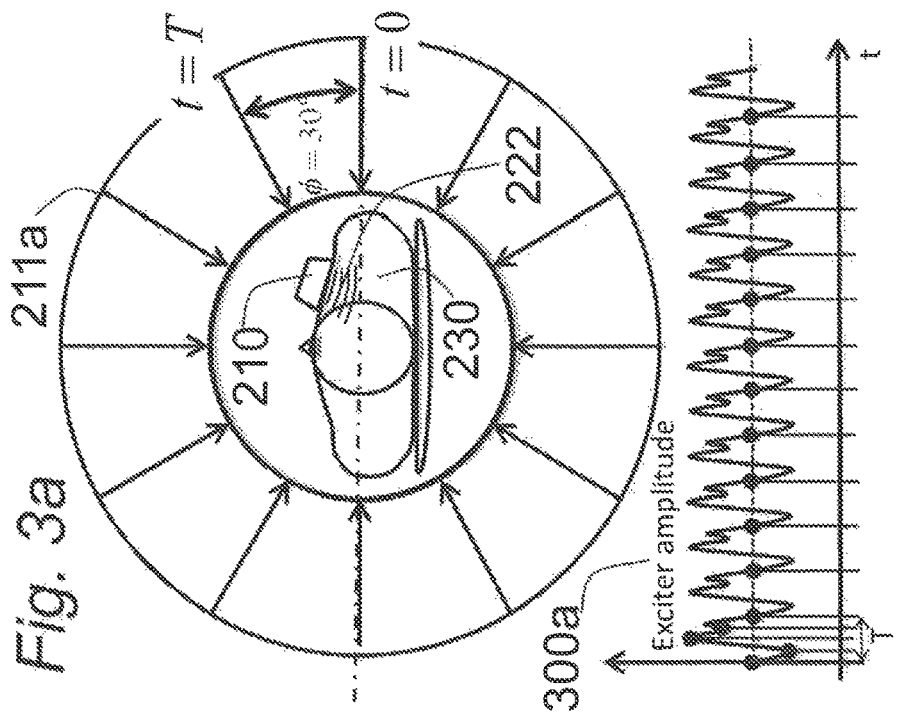

DYNAMIC COMPUTED TOMOGRAPHY IMAGING OF ELASTICITY

TECHNICAL FIELD

The present disclosure relates to the measurement of mechanical properties of tissue, also known as elastography, using an X-ray computed tomography (CT) scanner.

BACKGROUND

Elastography imaging can be thought of as a form of objective medical palpation, a medical technique that is commonly used by medical doctors to diagnose disease. Through palpation, stiffer, asymmetric, significantly heterogeneous, or otherwise abnormal tissue can be felt and is often indicative of diseases—as found in liver, prostate or breast malignancies.

The quantity depicted or inferred through elastography is elasticity. Elasticity is also referred to as stiffness, or the inverse of compliance. Elastography techniques can also measure the viscoelastic properties of tissue, such as viscosity and relaxation time. In elastography, a mechanical excitation is applied in the proximity of the tissue of interest, such as prostate, breast, liver or any other soft organ in the body, and the resulting deformation is measured. The resulting deformation is typically measured with ultrasound (the method known as ultrasound elastography or USE) or Magnetic Resonance Imaging (the method known as magnetic resonance elastography or MRE), as these imaging modalities do not involve the use of ionizing radiation. The deformation is post-processed to extract information such as viscoelastic properties (e.g., shear modulus and viscosity). The relative deformation or tissue strain, or alternatively, the intrinsic mechanical properties of tissue, can be displayed as a map of stiffness (or other meaningful mechanical properties) of the imaged object.

The main advantage of MRE is that it creates high quality quantitative images of the mechanical properties of tissue based on all displacement directions, and that the MR elastography images can be registered and superimposed onto other MR modalities such as T2-weighted imaging, that are excellent descriptors of anatomy or function. The problem with MRI is that MRI is a relatively slow imaging modality, so MRE typically requires many minutes of acquisition time.

Ultrasound provides faster acquisition yet it poses other challenges to overcome due to the pulse-echo nature of data acquisition and need for multiple pulses, which introduce time delays from both time of flight of the pulses and the delays between pulses in conventional ultrasound machines. Furthermore, tissue motion, as captured by an ultrasound transducer, usually represents the motion in the axial direction with respect to the ultrasound transducer, as the resolution of an ultrasound image is generally highest in the axial direction and lowest in the elevational direction, so tissue motion in the axial direction is measured with the highest accuracy. The other directions—lateral and elevational—are not as accurate. Ultrasound has a limited field of view and is not able to easily map the full abdominal cavity. Furthermore, the tissue contrast provided by standard ultrasound images, while also registered to elasticity images, is much poorer than for MRI.

SUMMARY

In the prior art, tissue elasticity imaging has been carried out primarily with ultrasound and MRI because these imaging modalities do not involve ionizing radiation. CT has not been widely used because elastography imaging involves deforming the tissue and imaging how it deforms, or how waves propagate through tissue.

For example X-ray CT elastography previously suggested in, for example, Liu et al, "Tomography-Based 3-D Anisotropic Elastography Using Boundary Measurements", *IEEE Trans. On Medical Imaging*, Vol. 24, no. 10, Oct. 2005 require that multiple full CT scans be performed on a patient. The patient is subjected to a full CT scan in each of different states of compression as in static elastography. Thus, at least two full CT scans must be performed according to prior art CT elastography methods, meaning that the ionizing radiation exposure that the patient is subjected to is at least double that of a conventional CT scan. Thus, the diagnostic power that might be gained by acquiring elastographic images may be offset by the increased risk of disease due to repeated radiation exposure due to the multiple full CT scans disclosed in the prior art.

The present disclosure describes X-ray computed tomography (CT) images that include information about tissue elasticity and viscosity. According to one aspect of the disclosure, a method is provided for imaging the mechanical properties of tissue utilizing a CT scanner. The method disclosed herein generates effective elastographic images while reducing the number of images taken compared to prior art methods, thus reducing the X-ray radiation exposure.

The present disclosure provides a system and method for CT elasticity imaging (CT Elastography or CTE) using a single conventional CT scan of a volume of tissue, and therefore does not expose a patient to a radiation dose that is significantly different than the radiation dose that is used in the conventional CT scan for the same volume of tissue.

The present disclosure provides a system and method for CT elasticity imaging (CT Elastography or CTE). CTE may be based on dynamic elastography, in which tissue deformation in response to a mechanical exciter is measured as a function of time by using specific subsets of the projections that are used in standard CT, but that are synchronized with specific states of the applied excitation. The disclosed system and method permit the application of a low level of radiation to the patient, similar to radiation levels inherently associated with conventional CT images, in the sense that the CTE images produced are co-localized with conventional CT images; provide 3D strain or quantitative elasticity based on 3D tissue deformation measurements; and can exploit the knowledge of tissue density acquired from basic CT in order to provide more accurate measurements of tissue elasticity than when other methods are used. The proposed method is fast, as CT image acquisition protocols utilized for the CTE are substantially similar to standard CT image acquisition protocols. Fast imaging improves the quality of elasticity images by reducing patient motion causes errors in the displacement maps of tissue during the imaging, which in turn may cause errors in the imaged elasticity values. CT is widely used for diagnostic imaging. The power of diagnostic imaging by CT could be increased by the addition of elasticity imaging to CT.

In an aspect, the disclosure provides a method of performing elastography of a volume of tissue of a patient with a CT scanner that includes applying, by a vibration source, periodic excitation waves to the volume of tissue, the periodic excitation wave having a plurality of phases that each correspond to a respective one of a plurality of deformation states of the volume of tissue, acquiring by the CT scanner a first plurality of CT projections at a first phase corresponding to a first deformation state of the volume of tissue, the first plurality of CT projections comprising a first CT projection set, acquiring by the CT scanner a second plurality of CT projections at a second phase corresponding to a second deformation state of the volume of tissue, wherein the second phase is different than the first phase, acquiring a second set of CT projections, the second plurality of CT projections comprising a second CT projection set, and determining, based on the first set of CT projections and the second set of CT projections, at least one of a tissue deformation field and a tissue mechanical property of the volume of tissue.

In another aspect, acquiring the first projection set and the second projection set include selecting at least one of an excitation wave period (T) of the vibration source and a CT scanner projection acquisition period ($T_S$) that satisfy $lT=kT_S$, where l and k are integers.

In another aspect, acquiring at least one of the first CT projection set and the second CT projection set further includes removing CT projections from the at least one of the first CT projection set and the second CT projection acquired outside of a gate window.

In another aspect, an excitation wave period is selected such that a heartbeat period of the patient is an integer number of the excitation wave period.

In another aspect, the gate window is determined based on at least one of an electro cardio gram (ECG) signal and a respiration rate of the patient.

In another aspect, determining includes determining a deformation field based on the first CT projection set and the second CT projection set.

In another aspect, determining includes determining a shear modulus of the volume of tissue based on the deformation field.

In another aspect, determining includes determining a change in the shear modulus as a function of frequency of the periodic excitation waves applied by the vibration source.

In another aspect, determining includes determining coherence between the excitation waves and the determined deformation field.

According to another aspect of the present disclosure, a system for performing elastography of a volume of tissue of a patient includes a computed tomography (CT) scanner having an X-ray source and detectors for generating CT projections of the volume of tissue, a vibration source for generating periodic excitation waves, a processor coupled to the CT scanner and the vibration source, the processor configured to apply, by the vibration source, periodic excitation waves to the volume of tissue, the periodic excitation wave having a plurality of phases that each correspond to a respective one of a plurality of deformation states of the volume of tissue, acquire, by the CT scanner, a first plurality of CT projections at a first phase corresponding to a first deformation state of the volume of tissue, the first plurality of CT projections comprising a first CT projection set, acquire, by the CT scanner, a second plurality of CT projections at a second phase corresponding to a second deformation state of the volume of tissue, wherein the second phase is different than the first phase, the second plurality of CT projections comprising a second CT projection set, and determine, based on the first set of CT projections and the second set of CT projections, at least one of a tissue deformation field and a tissue mechanical property of the volume of tissue.

According to another aspect of the present disclosure, a method is provided concurrently obtaining a CT image and a tissue deformation field of a volume of tissue undergoing a deformation includes acquiring, by the CT scanner, at least a first CT projection set corresponding to a first deformation state of the volume of tissue, deforming the volume of tissue to generate a second deformation state in the volume of tissue, acquiring a second CT projection set corresponding to the second deformation state of the volume of tissue, reconstructing a first CT image of the volume of tissue based on the first projection set, and a second CT image based on the second projection set, determining the tissue deformation field based on the first CT image and the second CT image, generating a modified second CT image by removing tissue deformation from the second CT image based on the tissue deformation field, and averaging the first CT image and the modified second CT image to generate an improved CT image.

BRIEF DESCRIPTION OF THE DRAWINGS

The following figures set forth embodiments in which like reference numerals denote like parts. Embodiments are illustrated by way of example and not by way of limitation in the accompanying figures.

FIG. 1a is a schematic view of an example CT scanner for detect a projection from a X-ray source according to the prior art;

FIG. 1b is a graph showing an example projection as a function (collection) of detector values determined by the CT scanner shown in FIG. 1a;

FIG. 2b is a graph showing an example exciter amplitude and projection angle as a function of time for the system shown in FIG. 2a;

FIGS. 3a-3d are schematic views of an example system for acquisition of CT projections synchronized with the exciter according to the embodiment shown in FIG. 2a, and graphs showing corresponding exciter amplitudes, at different tissue phases;

DETAILED DESCRIPTION

Figure 2A:
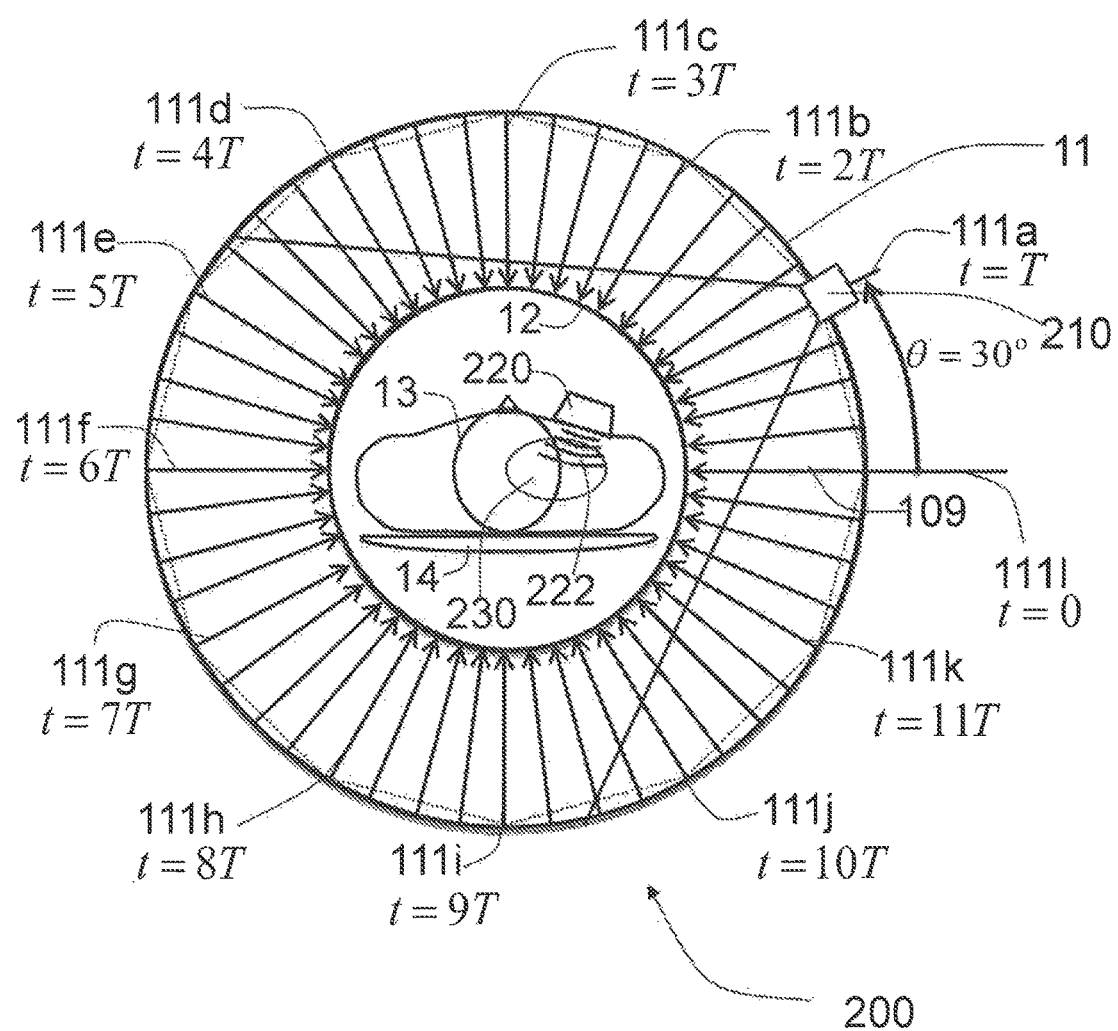
FIG. 2a is a schematic view of an example system for acquisition of CT projections synchronized with an external exciter according to an embodiment.

For simplicity and clarity of illustration, reference numerals may be repeated among the figures to indicate corresponding or analogous elements. Numerous details are set forth to provide an understanding of the examples described herein. The examples may be practiced without these details. In other instances, well-known methods, procedures, and components are not described in detail to avoid obscuring the examples described. The description is not to be considered as limited to the scope of the examples described herein.

Conventional CT is an established technique for medical imaging that is described in, for example, J. T. Bushberg et al, "The essential physics of medical imaging", and references included therein. Essentially, CT imaging of a volume of tissue involves (i) the acquisition of many X-ray images or "projections" of the volume of tissue as an X-ray source rotates around it. Each projection is dependent on the X-ray attenuation in the volume of tissue being imaged. After acquisition, a reconstruction, from these projections, is performed of the spatial distribution of X-ray attenuation in the volume of tissue being imaged.

With reference to FIGS. 1a and 1b, CT projection acquisition utilizing CT scanner is described. The specific geometry and beam shape presented here are for illustration only. In the example shown, an X-ray source 210 rotates along a circular trajectory 11 and images a cylindrical region 12 containing a patient 13 lying on a table 14. The rotating X-ray source 210 generates a fanned X-ray beam 15 spanning an angle range $\varphi$ from a source direction 111 with a range of $[-\varphi_{max}, \varphi_{max}]$. An array of Detectors 20 rotate with the X-ray source 210 and detect the intensity of the fanned beam 15 rays that impinge upon them. In other examples, detectors may be stationary and distributed along a full circle surrounding the cylindrical region 12. In the example shown in FIG. 1a, seven detectors 20a-g are included in the array with rays impinging upon them. However any number of detectors may be included. The intensity data from the detectors 20 are assembled into a projection $p(\theta)$, which is a set of discrete detected intensities at each detector. Seven of the detected intensities, 21a-g, shown in the graph in FIG. 1b, corresponding to respective detectors 20a-g.

For simplicity of exposition, in the description and the figures, each projection $p(\theta)$ is described according to its source direction (111 in FIG. 1b). In this disclosure, a projection $p(\theta)$ and its associated direction 111 may be used interchangeably.

FIG. 2a shows an example of a CT scanning device 200 that is configured for performing elastography measurements. The example CT scanning device 200 is illustrated with 48 source directions, each represented by an arrow pointing from the circular trajectory 11 to the inner cylinder 12. Each of the 48 source directions correspond with a respective one of 48 projections $p(\theta)$, $\theta=k \cdot 7.5°$, where $k=1, \ldots, 48$ acquired by the array of CT detectors (not shown). The source 210 in the example device shown FIG. 2a is shown at a source direction 111a at an angle $\theta=30°$ from horizontal, corresponding to four increments of 7.5° with respect to the horizontal. Typically, for fan-beam CT devices, there are between 1000 and 2000 different projections. Although the source 210 of the example scanner 200 shown in FIG. 2a is configured to perform a complete rotation around the patient 13, typically modern CT scanners may use a maximum rotation angle of $\theta=180°$ for the source 210 plus the angle of the fanned beam (identified as 15 in FIG. 1a).

Normally, the CT number or Hounsfield unit, proportional to the difference between tissue X-ray attenuation and water X-ray attenuation, normalized to water X-ray attenuation, is displayed as an image. The principles of CT image reconstruction from a set of projections are well understood and are therefore not further described herein. An algorithm called "filtered back-projection" may be used for CT reconstruction. In this algorithm, the projections are filtered with a spatial filter and then they are back-projected to the same volume of tissue they traversed.

Alternatively, an "algebraic reconstruction" may be used in which discretization of the imaged volume into voxels is performed, with the voxel X-ray attenuation or CT number as the unknown for each of the voxels. Then each source-detector ray line provides one equation equating the sum of attenuations for the voxels in that line to the intensity read by the detector. The CT image is found by solving a large linear algebraic system of equations in which each equation arises by equating the sum of attenuations of the voxels traversed by a ray with the detected intensity corresponding to that ray. The more detectors that are utilized results in more projections and more equations that are utilized, resulting in a better image.

For illustration, a CT scanner with planar fan-beam geometry has been used in the FIGS. 1.a, 2.a, and 3.a,b,c,d. Parallel-beam or cone-beam geometries can be treated in a similar manner. It would be understood by those skilled in the art that the example approach described herein utilizing 2D fan-beam geometry may be similarly applied to a 3D reconstruction, regardless of how the 3D reconstruction is achieved. 3D reconstruction may be achieved utilizing, for example, slice-by-slice reconstruction, multiple detector arrays, spiral CT with interpolation, or any other means known in the art, used in combination or independently.

In the example shown in FIG. 2a, an external exciter 220 is used as a vibration source for elastography imaging. The excitation waves, denoted by lines 222, created by the external exciter 220 propagate through the tissue of the patient 13. The patient 13 may be, for example, a human, an animal, a tissue phantom, or any other material imaged in vivo or in vitro. In this example shown, the patient 13 is shown lying supine on a bed 14, with the exciter 220 placed on the abdomen. The exciter 220 could be driven by any type of suitable actuator that can produce mechanical excitation in the 1-1000 Hz range. Examples of suitable actuators for the exciter 220 include actuators that utilize electrodynamic actuation, voice coils, and piezoelectric actuation. The exciter 220 may utilize any suitable type of transmission to the patient including, for example, a rigid link, bar, geared, cam, pneumatic, or hydraulic transmission. The transmission of the exciter 220 may be selected to avoid having a metallic object in the way of the X-ray beam which may generate CT imaging artefacts. In other examples, high intensity acoustic radiation forces generated by a specialized device may be utilized to generate internal tissue motion rather than the exciter 220 shown in FIG. 2a.

Figure 8:
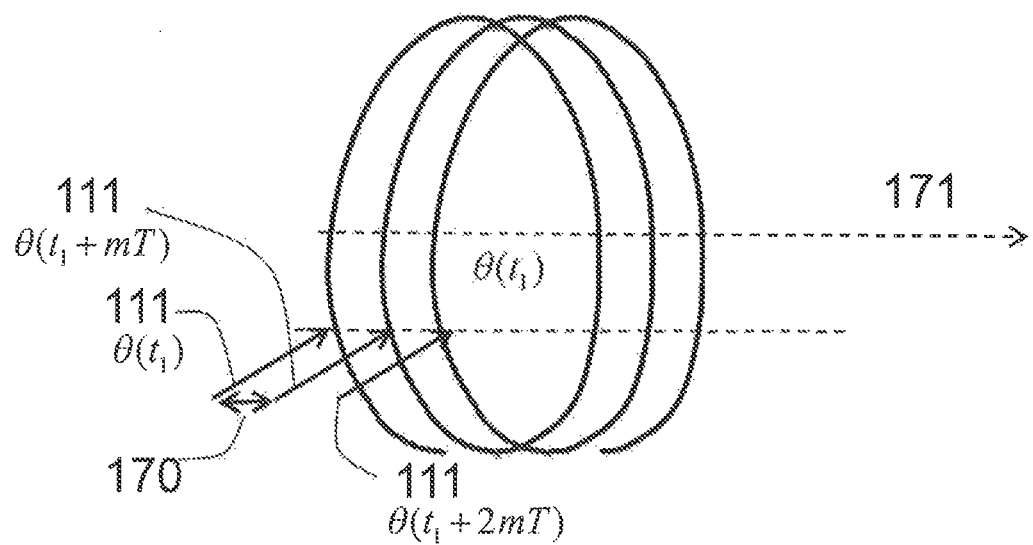
FIG. 8 is a schematic diagram illustrating an example spiral CT synchronization of table pitch to projection acquisition in a system for acquisition of CT projections according to another embodiment.

A processor (not shown) may be coupled to the X-ray source 210, the exciter 220, and detectors (not shown) to control the acquisition of the CTE images by the CT scanner 200, similar to the example described in more detail below with reference to FIG. 8.

Lung and cardiac tomography have motivated the development of "4D CT", which can show human body volumes (3-dimensional regions or 3D), as a function of time (the fourth "dimension" of 4D CT), as the imaged volume changes during a respiratory cycle or a cardiac cycle. With modern scanners, the temporal resolution has become sufficiently high to reconstruct one or more specific phases of the beating heart or the respiratory cycle by electrocardiogram (ECG) or respiratory gating. This development is described, for example, in the following references which are hereby incorporated by reference: J. Ehrhardt, et al., An optical flow based method for improved reconstruction of 4D CT data sets acquired during free breathing, *Med. Phys.* 34 (2) (2007) 711-721, T. Pan, et al., 4D-CT imaging of a volume influenced by respiratory motion on multi-slice CT, *Med. Phys.* 31 (2), (2004) 333-340, and G. Wang, S. Y. Zhao, D. Heuscher, A knowledge-based cone-beam X-ray CT algorithm for dynamic volumetric cardiac imaging, *Med. Phys.* 29 (8) (2002) 1807-1822).

Figure 2B:
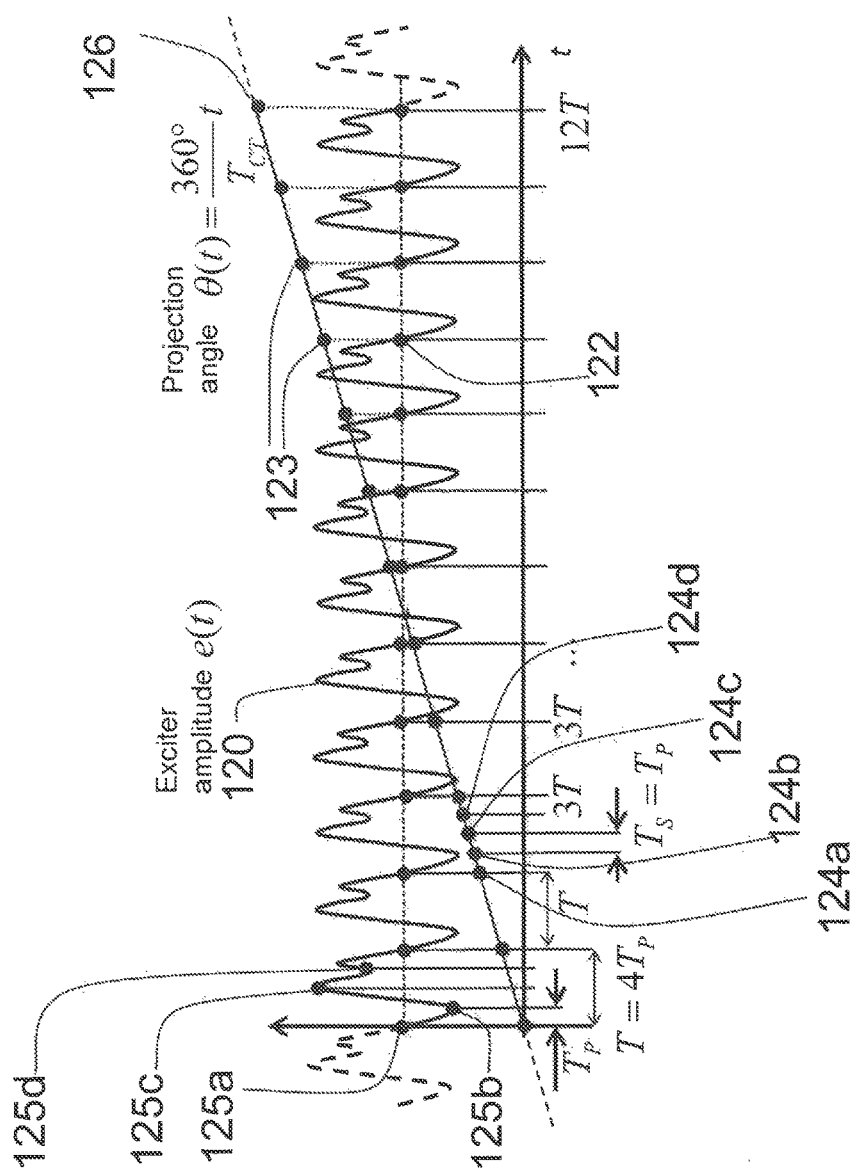

The CT projection acquisition sequence for elastography may be, for example, a "4D CT" projection acquisition sequence that is synchronized with a periodic mechanical excitation. FIG. 2b shows a graph 120 of the exciter amplitude, e(t), as a periodic function of time. The term "periodic" as used herein means a function having a graph that repeats after a fixed interval (period), i.e a function of time $f(t)$ is "periodic" with period T if $f(t)=f(t+T)$ for any time t.

The exciter amplitude curve 120 may be defined in terms of, for example, force, torque, displacement, angle, exciter voltage, actuator current, air pressure, hydraulic pressure. The exciter 220 may be computer controlled and designed in such a way as to generate a controlled excitation onto the tissue to generate a harmonic excitation. For example the harmonic excitation may be a single sinusoidal excitation of the form A cos($\omega$t) for a given frequency $\omega=2\pi f$ rad/s, or may be a sum $\Sigma A_i \cos(\omega_i t + \alpha_i)$ of multiple harmonics at different frequencies $\omega_i$ Hz and with different phase offsets $\alpha_i$. The excitation is periodic, with period T, i.e., e(t+T)=e(t) for all t. It is understood that if T is the period of the signal, then so is any integer multiple of T; therefore reference to the function period means a reference to the values of T for which e(t+T)=e(t) for all t, which is usually the smallest multiple of T.

In order to measure the elastic properties of the tissue within a volume of interest, such as the volume 230 illustrated in FIG. 2a, it may be desirable to determine the tissue deformation in response to the mechanical excitation in that volume of interest 230. Assuming there are no other sources of tissue motion other than the exciter 220, when the excitation is periodic the tissue deformation in the volume of interest 230 is expected to eventually settle into a motion pattern that is also periodic with the same period T Techniques utilized to reduce or compensate for imaging artefacts that are caused by other motion sources, such as for example breathing and heartbeat motion, that may interfere with the periodic excitation generated by the exciter 220 are described in more detail below.

For a periodic amplitude of the exciter 220, such as exciter amplitude 120 shown in FIG. 2b, the signal of the mechanical exciter 220 can be synchronized with the acquisition of the projection data. Synchronizing the projection acquisition with the exciter 220 enables a set of projections to be acquired at the same phase of the exciter signal 120. In this way all of the acquired projections of the set are of the same deformation state corresponding to the same state or phase of the excitation period. The state or phase of the periodic signal at time t may be defined to be the delay, up to a signal period T relative to a time origin t=0, or the minimum positive t−mT over the integer m. FIG. 2b illustrates four equally spaced phases or delays of the periodic exciter amplitude 120 e(t), separated from each other by a time period $T_P$, as illustrated by points 125a, 125b, 125c, and 125d in FIG. 2b, wherein: the point 125a corresponds to t=0, e(0); the point 125b corresponds to t=$T_P$, e($T_P$); the point 125c corresponds to t=2$T_P$, e(2$T_P$); and point 125d corresponds to t=3$T_P$, e(3$T_P$). In this case the period of the signal 120 is T=4$T_P$.

If the excitation is a periodic signal, and if each projection in a set is acquired at the same phase of the excitation, the projections will correspond to the same tissue deformation state. For strain or elasticity measurement, at least two sets of projections are utilized to image a deformation between states. As used herein, a set of projections means a plurality of individual projects that are taken at approximately the same phase of the periodic excitation signal. Each of these sets of projections may be acquired sequentially.

For example, a first set of projections may include a plurality of individual projections that are each acquired at approximately the same first phase $T_a$ of the periodic excitation signal, and a second set of projections may include a plurality of individual projections that are each acquired at approximately the same second phase $T_b$ of the excitation signal, where $T_a$ and $T_b$ are different phases. In this manner, acquisition of the projections of a set of projections is synchronized with the excitation signal. In other examples, more than two sets of projections may be acquired, which each set of projections corresponding to a different phase of the excitation signal.

Alternatively, rather than an exciter 210 applying a periodic excitation wave as shown in FIGS. 2a and 2b, quasi-static CT elastography may be performed in which a first portion of the projections of the CT scan are acquired with the tissue in a first deformation state, and another second portion of projections of the CT scan are acquired when the tissue is in a second deformation state. For example, the first deformation state may be the result of having no external force applied to the tissue and the second deformation state may be the result of having a static, or quasi-static, force applied to tissue to cause a static or quasi-static deformation relative to tissue with no applied external force. The external force may be applied to tissue by any suitable means including, for example, an inflatable sac that contains the volume of tissue similar to, for example, a blood pressure arm band. For example, the first deformation state may be the state of the tissue when the inflatable sac is deflated, thus applying no, or little, pressure to the volume of tissue. The second deformation state may be the state of the tissue when the inflatable sac is inflated such that the inflatable sac applies a pressure that compresses the tissue. The first portion and the second portion of the projections of the CT scan may be then be analyzed to produce a tissue deformation field and CT image as described in more detail below.

Referring back to FIGS. 2a and 2b, an illustrative example of acquiring sets of projections that are synchronized with a particular phases of the mechanical excitation is described for the case in which: (i) the angle θ(t) of the source 210 is increasing linearly with time t as the function graph 126, with $\theta(t)=[360°/T_{CT}]t$ degrees, with a constant angular velocity $[360°/T_{CT}]$ degrees per second, where $T_{CT}$ is the period of rotation of the source in seconds; (ii) the excitation e(t) is periodic, with the tissue motion within the volume of interest 230 being in steady state and therefore periodic (the origin t=0 chosen arbitrarily); and (iii) the CT are acquired every $T_S=T_{CT}/N_{CT}$ seconds, where $N_{CT}$ is the total number of projections acquired per CT source revolution.

In this example, one choice for the mechanical excitation to be synchronized with the CT projection acquisition is to select the mechanical exciter period T to be an integer multiple of the projection sampling period $T_S$, i. e., $T=kT_S$, k=1, 2, 3, . . . . Preferably k is equal to or larger than 2, in order to capture at least two tissue deformation states. If at least two deformation states are captured and the tissue has settled into a periodic motion, the projections that are acquired at the specific sampling times $t=kT_S$, $t=2kT_S$, . . . , $t=N_{views}kT_S$, given by p(θ(T)), p(θ(2T)), . . . p(θ($N_{views}$T)), form a set that correspond to the same state of the mechanical excitation signal e(T), e(2T), . . . e($N_{views}$T), which are all the same as e(0).

A specific case of such a choice $T=kT_S$, k=4 is illustrated in FIGS. 2a and 2b, where $N_{CT}$=48 and $N_{views}$=12. In FIG. 2b, the projections that are sampled for this case between time t=2T and time t=3T are illustrated as the dots 124a, 124b, 124c, 124d along the linear graph 126 of the projection angle, acquired at sampling instances that correspond to the different phases 125a, 125b, 125c, 125d of the exciter amplitude. In FIG. 2a, the projections acquired at these samples $t=4T_S$=T, $t=8T_S$=2T, . . . , $t=48T_S$=12T correspond respectively to projections acquired with the source 210 being located at directions 111a, t=T, θ=30°, 111b, t=2T, θ=60°, 111c, t=3T, θ=90°, 111d, t=4T, θ=120°, 111e, t=5T, θ=150°, . . . 111l, t=12T, θ=360°, for which the tissue being imaged is in the same deformation state corresponding to e(0), because the time difference between consecutive projections is equal to the period T of the exciter amplitude. Thus, of the $N_{CT}$=48 projections p(θ($T_S$)), p(θ(2$T_S$)), p(θ($N_{CT}T_S$)) that are shown in FIG. 2a that are available for the CT reconstruction of the volume of interest 230 as waves 222 propagate through it, there are $N_{views}$=12 projections p(θ(4$T_S$)), p(θ (8$T_S$)), p(θ(12$T_S$)), . . . p(θ(48$T_S$)), or 111a, 111b, 111c, 111d, 111e, 111f, 111g, 111h, 111i, 111j, 111k, 111l, that form a projection set (211a, FIG. 3a) for which the tissue state is the same as it was at t=0.

In order to characterize tissue strain or elasticity, there must be at least another projection set acquired over time at a different exciter phase, for which the tissue is in another deformation state. The example of FIG. 2b shows $N_{phases}$=4 equally dispersed time phases 125a, 125b, 125c, 125d per exciter amplitude period T, with $T=N_{phases}T_P$=4$T_P$.

Figure 3D:
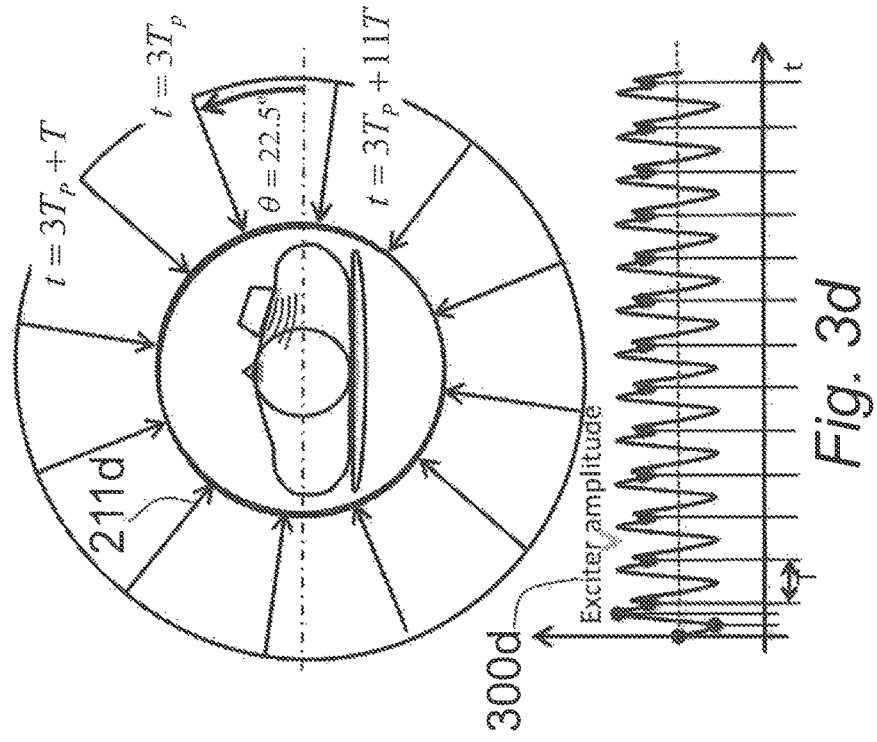
Figure 3C:
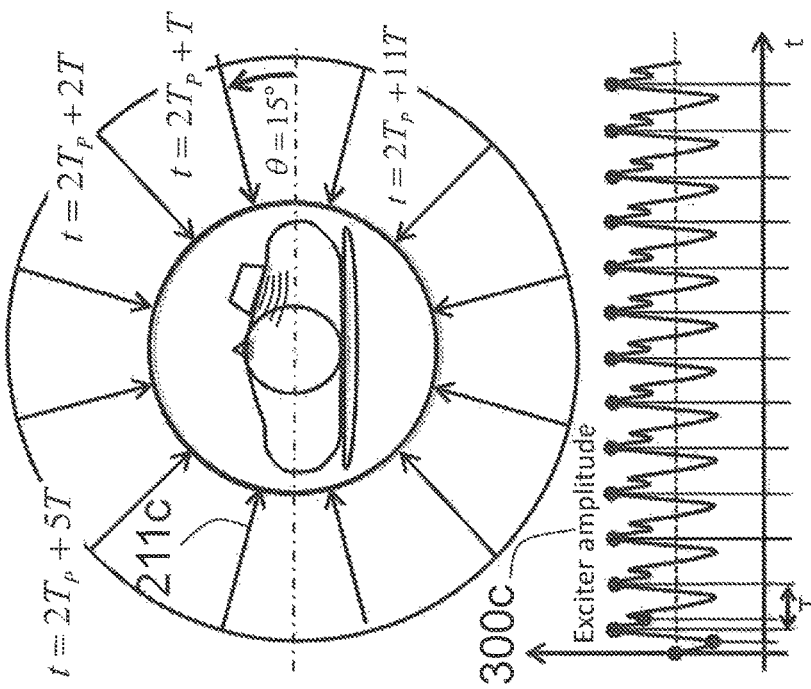

FIG. 3 shows an example in which $N_{phases}$=4 sets of $N_{views}$=12 projection sets that are acquired at these phases. In particular, in the example shown in FIG. 3a a first projection set 211a is acquired for t=T, t=2T, t=3T, . . . , $t=N_{views}T$, with a set of acquired projections {p(θ(T)), p(θ(2T)), . . . p(θ($N_{views}$T))}, for which the tissue deformation state corresponds to the excitation being in state e(0) (phase 125a of FIG. 2b, phases 300a in FIG. 3a). As shown in FIG. 3b, a second projection set 211b is acquired for $t=T_P+T$, $t=T_P+2T$, $t=T_P+3T$, . . . , $t=T_P+N_{views}T$, with a set of acquired projections {p(θ($T_P$+T)), p(θ($T_P$+2T)), . . . p(θ($T_P+N_{views}$T))} for which the tissue deformation state corresponds to the excitation being in the state e($T_P$) (phase 125b of FIG. 2b, phases 300b in FIG. 3b). As shown in FIG. 3c, a third projection set 211c is acquired for $t=2T_P$ T, $t=2T_P+2T$, $t=2T_P+3T$, . . . , $t=2T_P+N_{views}T$, with a set of acquired projections {p(θ(2$T_P$+T)), p(θ(2$T_P$+2T)), . . . p(θ (2$T_P+N_{views}$T))} for which the tissue deformation state corresponds to the excitation being in the state e(2$T_P$) (phase 125c in FIG. 2b, phases 300c in FIG. 3c). As shown in FIG. 3d, a fourth projection set 211d is acquired for $t=3T_P+T$, $t=3T_P+2T$, $t=3T_P+3T$, . . . , $t=3T_P+N_{views}T$ with a set of acquired projections {p(θ(3$T_P$+T)), p(θ(3$T_P$+2T)), . . . p(θ (3$T_P+N_{views}$T))} for which the tissue deformation state corresponds to the excitation being in the state e(3$T_P$) (phase 125d in FIG. 2b, phases 300d in FIG. 3d).

In the above example, and the example illustrated in FIG. 2b, the number of phases $N_{phases}$ of the mechanical exciter 220 is selected to be equal to the number of projections acquired for each phase, and the phase sampling time to be the same as the projection sampling time, or $T_P=T_S$, but this does not necessarily have to be the case. For example, only two phases or states could have been acquired by setting $T_P=2T_S$ instead of $T_P=T_S$.

For each of the sets of projections 211a, 211b, 211c, 211d in FIG. 3a, FIG. 3b, FIG. 3c, FIG. 3d, respectively, the exciter and therefore the imaged tissue volume is in the same state of deformation. From all of the $N_{CT}$=48 of projections shown in FIG. 2a that are available for the CT reconstruction of the volume of interest 230 as waves propagate through it, there are four sets of $N_{views}$=12 projections that are acquired for which the tissue is in one of the $N_{phases}$=4 states corresponding to the excitation states e(0), e($T_P$), e(2$T_P$), e(3$T_P$).

In FIG. 3b, the set of acquired projections in set 211b are offset by an angle θ=7.5° with respect to those in set 211a of FIG. 3a. In FIG. 3c, the set of acquired projections 211c are offset by an angle θ=15° with respect to those in set 211a of FIG. 3a. In FIG. 3d, the set of acquired projections 211d are offset by an angle θ=22.5° with respect to those in set 211a of FIG. 3a.

In general, there are trade-offs involved in the selection of the tissue exciter period T, the number of phases $N_{phases}$, the period of rotation $T_{CT}$ of the source 210, and $N_{CT}$, the total number of projections acquired per revolution (or equivalently, $T_S=T_{CT}/N_{CT}$, assuming constant sampling time $T_S$). For simplicity we consider the case in which the source rotation is constant (the angle varies linearly with time as in FIG. 2.b), and there is a constant time delay $T_P$ between acquired tissue deformation states. These are related as in equation (1):

$$\frac{T_{CT}}{T} = \frac{N_{CT}}{N_{phases}} = N_{views} \geq N_{min} \quad (1)$$

where $N_{CT}$ is the number of projections acquired by the CT scanner in a full rotation.

Typically, a lower bound $N_{min}$ on the minimum number of projections $N_{views}$ per tissue deformation phase is desired because the higher the number of projections in a CT reconstruction, the more accurate the reconstructed tissue image. If the number of phases $N_{phases}$ is too large, there will be too few views for CT reconstruction. Therefore, we also expect that the period of mechanical excitation that we can apply to tissue to be bounded by $$T = \frac{N_{phases}}{N_{CT}} T_{CT} \leq \frac{T_{CT}}{N_{min}} \quad (2)$$

and correspondingly, that the frequency of excitation is limited by $$f = \frac{1}{T} = \frac{N_{CT}}{N_{phases}} \frac{1}{T_{CT}} \geq \frac{N_{min}}{T_{CT}} \text{ Hz} \quad (3)$$

The following table illustrates the above requirement by displaying the lowest frequency of excitation $f$ in Hertz corresponding to equation (3), for $T_{CT}$ in seconds (columns 3-7), and for different number of equidistributed phases $N_{phases}$ throughout the signal period T (rows 3-7). The total number of projections per source revolution is assumed to be equal to $N_{CT}$=1000.

| $N_{phases}$ | $N_{views}$ | $T_{CT}(s)$ | 0.25 | 0.5 | 1 | 2 | 5 | 10 |
|---|---|---|---|---|---|---|---|---|
| 4 | 250 | | 1000 | 500 | 250 | 125 | 50 | 25 |
| 5 | 200 | | 800 | 400 | 200 | 100 | 40 | 20 |
| 8 | 125 | | 500 | 250 | 125 | 62.5 | 25 | 12.5 |
| 10 | 100 | | 400 | 200 | 100 | 50 | 20 | 10 |
| 20 | 50 | | 200 | 100 | 50 | 25 | 10 | 5 |

The above table shows that with reasonable adjustment of the source rotation time (0.25 seconds is slightly faster than what state-of-the-art machines are capable of achieving), to reasonably long source rotation (10 seconds), and from 4 to 20 phases per period of excitation, corresponding to a number of projections acquired with identical tissue state or phase ranging from 250 down to 50, the minimum frequency of excitation ranges from 1000 Hz to 5 Hz. Human body elastography results have been reported over this range of frequencies, with strain displayed at the lower range and quantitative images of the shear modulus displayed in the 200 to 800 Hz. The selection of scanning parameters can be experimentally determined within this range of 5 Hz to 1000 Hz in order to obtain a good depth of penetration and a high spatial resolution of the tissue elasticity properties.

From the table above it can be seen that at typical CT scanner rotation speeds currently in use, it is possible to cover a range of mechanical exciter frequencies that is useful in elastography with several tissue states and with a minimum number of projections per state, so that each state can be reconstructed with good accuracy.

Nevertheless, further flexibility in the choice of how the CT projection acquisition is synchronized with the exciter may be enabled by utilizing the fact that that if the mechanical excitation is periodic with period T, it is also periodic with period lT, for any integer l. This periodicity can be used to sample high frequency tissue motion generated by the mechanical exciter at a lower sampling frequency, by selecting a scanner projection acquisition period $T_S$ and an excitation period T such that $lT=kT_S$, where k=1, 2, 3, . . . , and l=1, 2, 3, . . . .

Figure 4:
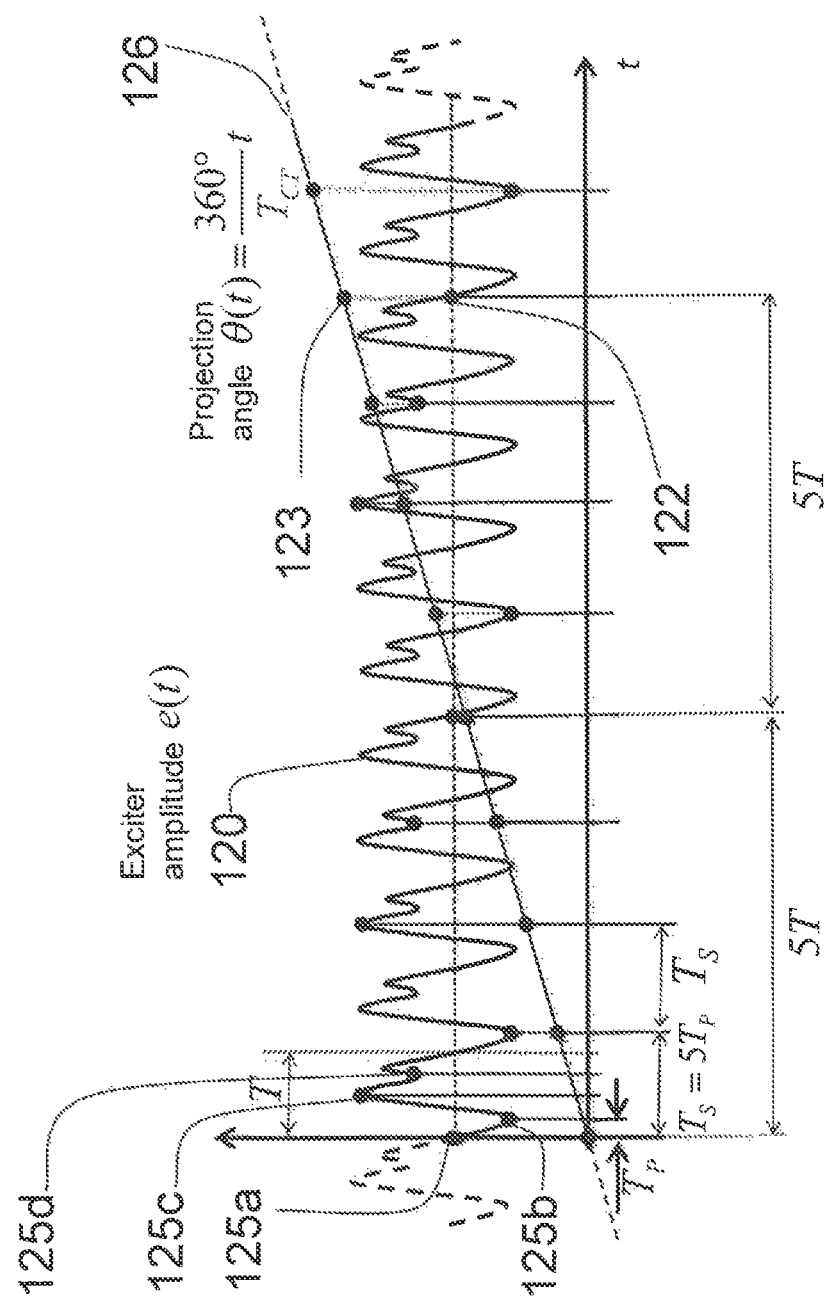
FIG. 4 is a graph showing an example exciter amplitude and projection angle as a function of time of an example acquisition of CT projections synchronized with the exciter according to another embodiment in which the time between projection acquisitions is larger than the period of the mechanical exciter.

In the example shown in FIG. 4, a periodic exciter signal 120 from FIG. 2b is utilized together with a scanner projection acquisition period $T_S$ that is larger than the smallest period T of the periodic exciter signal, i.e., $T_S$=5/4T. A new term $T_P$ such that T=4$T_P$ and $T_S$=5$T_P$ may be defined, where $T_P$ represents the period of the phases within the periodic exciter signal e(t) (120 in FIG. 2b). Thus, if the scanner projection acquisition period is set such that 5T=4$T_S$, then the sampling period is $T_S$=5/4 T=5$T_P$, then the sampling points 122 sample projections angles 123 for which the same tissue states or phases correspond to the excitation states e(0), e($T_P$), e(2$T_P$), e(3$T_P$), as shown in FIG. 2b and FIG. 3. Indeed, at time t=0, we sample the tissue phase corresponding to exciter phase 125a or e(0), at time t=$T_S$=5$T_P$ we sample the tissue phase corresponding to exciter phase 125b or e(5$T_P$)=e(5$T_P$−T)=e($T_P$), at time t=2$T_S$=10$T_P$, we sample the tissue phase corresponding to exciter phase 125c or e(10$T_P$)=e(10$T_P$−2T)=e(2$T_P$), and at time t=3$T_S$=15$T_P$, we sample the tissue phase corresponding to exciter phase 125d or e(15$T_P$−3T)=e(3$T_P$), and so on. As explained before, the projections corresponding to different exciter phases can be grouped together into projection sets that correspond to the same tissue deformation states.

To summarize, if the CT imager projection acquisition sampling time $T_S$ is related to the period T of the mechanical exciter according to lT=k$T_S$, k=1, 2, 3, . . . , l=1, 2, 3, . . . , then there will be a set of CT imager projections that are acquired with the excited tissue being in exactly the same deformation state or phase. This requirement is equivalent with the ratio of the mechanical exciter period T to the CT scanner projection sampling period $T_S$ being the ratio of two integers:

$$\frac{T}{T_S} = \frac{k}{l}, \quad (4)$$

where $k = 1, 2, 3$ and $l = 1, 2, 3$ are integers

Figure 5:
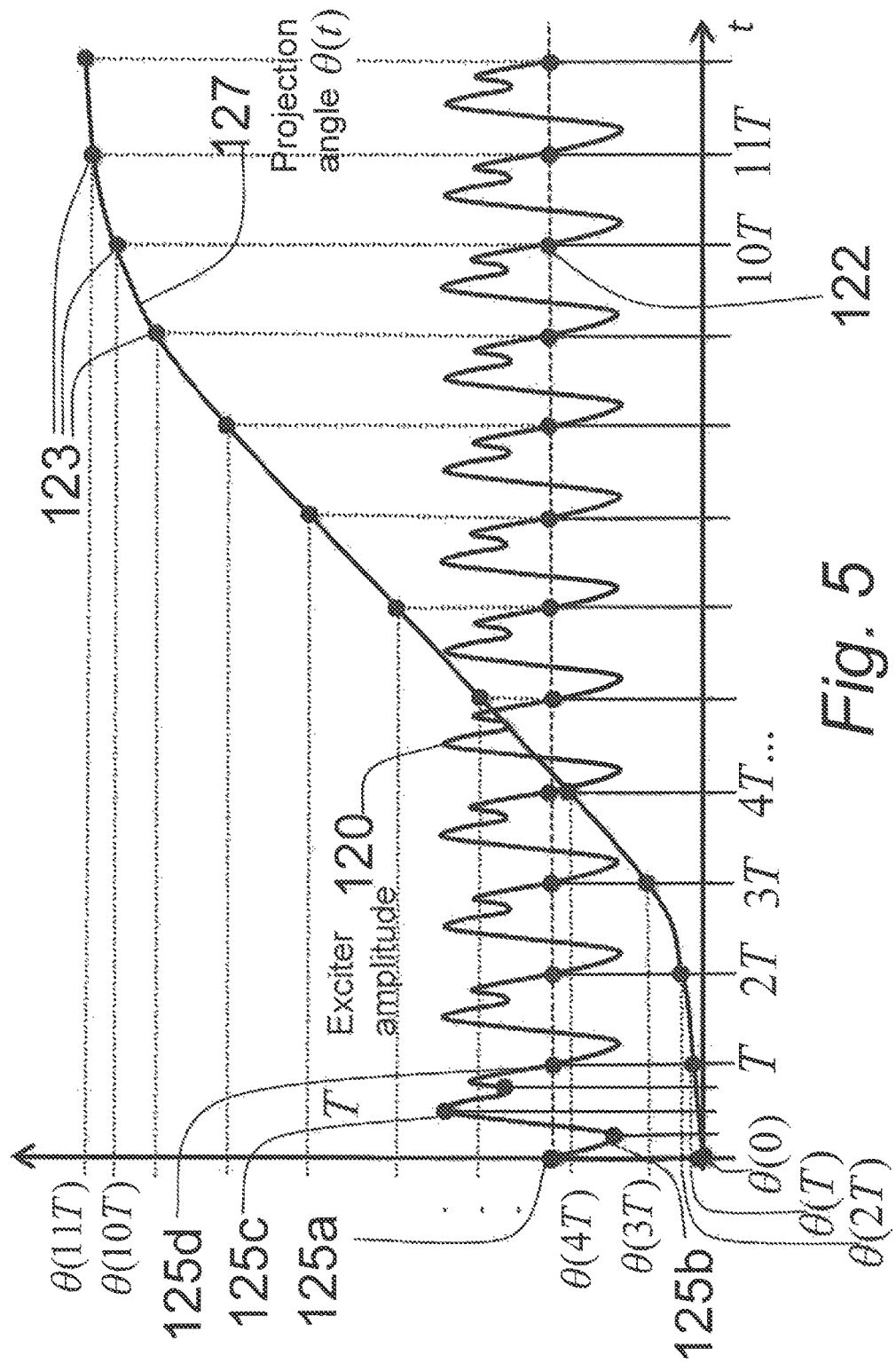
FIG. 5 is a graph showing an example exciter amplitude and projection angle as a function of time of an example acquisition of CT projections synchronized with the exciter according to another embodiment in which the source angular velocity is not constant.

In general, there is no requirement that the source projection angle θ(t) be increasing linearly with t as shown in, for example, the function graph 126 in FIGS. 2b and 4. This type of source trajectory was utilized in the described examples to simplify the description and to recognize that in order to keep scanning time small, the X-ray source should rotate at its maximum rotation speed, so in most cases this will be constant. As illustrated in FIG. 5, a set of projections that correspond to a particular tissue deformation state or phase can be obtained for an arbitrary source angle trajectory by sampling the angle trajectory 127 at the period T of the exciter amplitude 120 (sampling points illustrated by dots 122). As shown in FIG. 5, the angles θ(0), θ(T), θ(2T), θ(3T), . . . , θ(10T), and θ(11T), denoted as a set as 123 in FIG. 5, are sampled from the source trajectory angle 127 at sampling points 122, for t=0, t=T, t=2T, t=3T, . . . , t=11T, define a set of projections that correspond to a particular tissue deformation state or phase (periodic repetition of the tissue state at t=0). This set of projections is not at equal angle increments with respect to each other, but can still be used for tissue CT image reconstruction.

Figure 6:
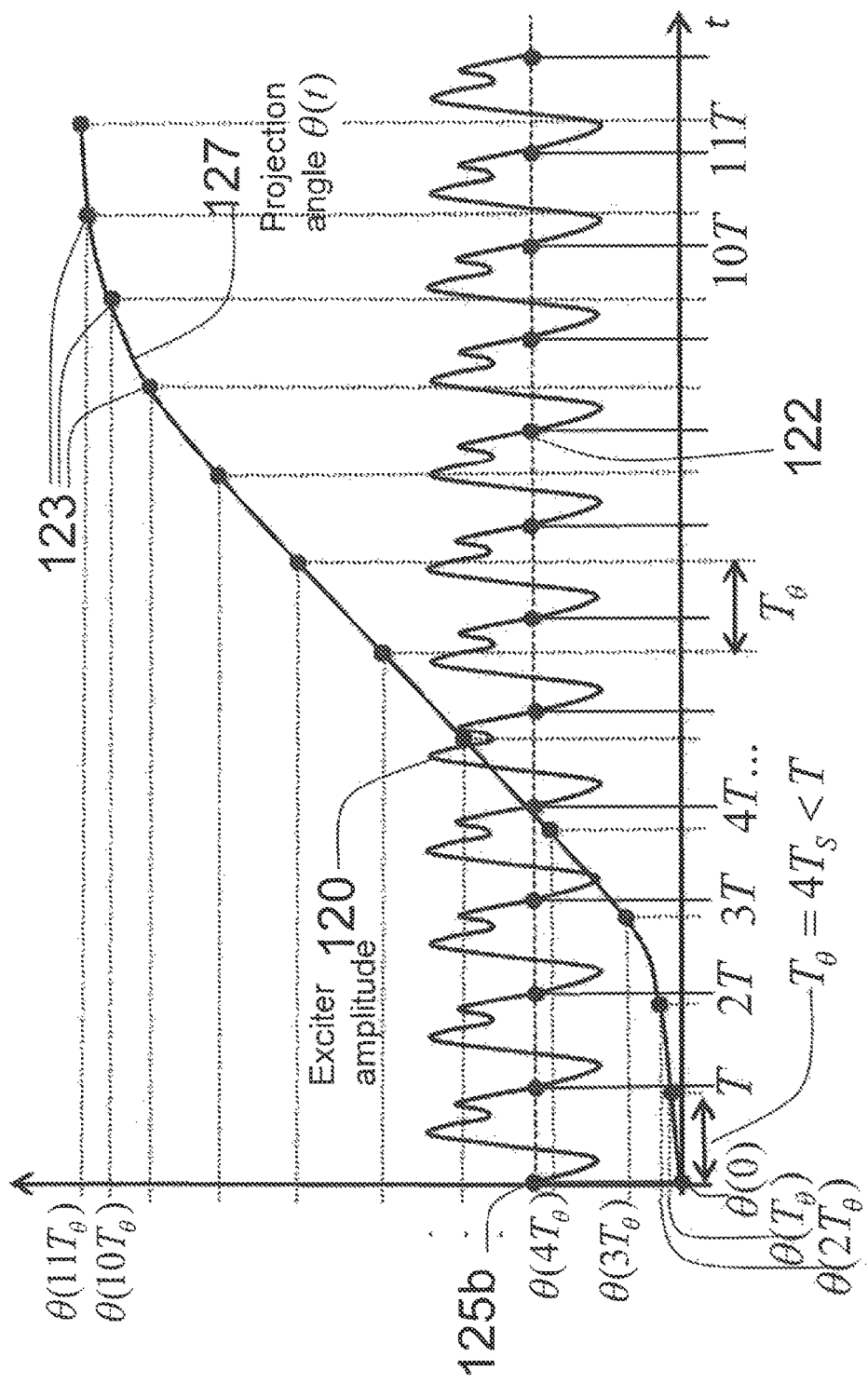
FIG. 6 is a graph showing an example exciter amplitude and projection angle as a function of time of an example acquisition of CT projections synchronized with the exciter according to another embodiment in which acquisition of CT projections are not synchronized to the phase of the exciter.

Small differences between the period of the mechanical exciter T and the time $T_θ$ between the projection acquisition samples that correspond to a given tissue phase can lead to loss of synchronization in which the set of projections acquired by the CT do not correspond to the same phase. FIG. 6 illustrates the case in which the time $T_θ$=4$T_S$<T, and shows that the projection angles 123 that is sampled at a sampling period $T_θ$ no longer correspond to the appropriate phase.

Figure 7:
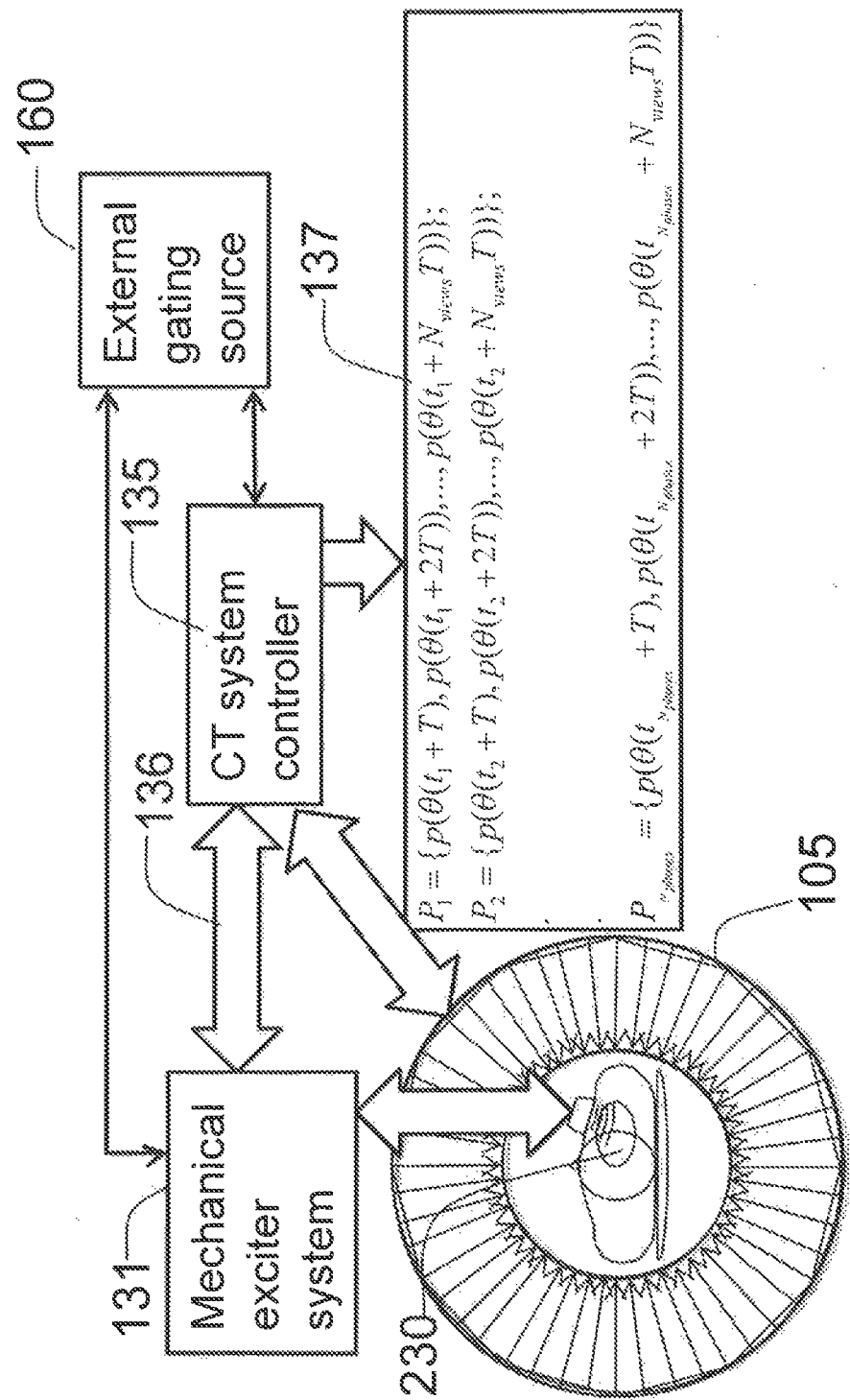
FIG. 7 is a schematic view of an example system for acquisition of CT projections according to another embodiment in which the CT projection acquisition is synchronized to the mechanical exciter signal.

As illustrated in FIG. 7, the synchronization of the projection sets of the volume of interest 230 that correspond to a particular tissue deformation state due to the mechanical exciter can be accomplished by a communications system 136 between the mechanical excitation controller 131 and the computer 135 that is controlling and gathering the projection data within a CT machine 105, which may be, for example, a CT scanner as described above with reference to FIGS. 1a and 2a. There are many ways in which such synchronization can be achieved through a communication system 136. For example, these may include: triggering projection acquisition of the CT machine at specific time intervals corresponding to the phases of the periodic excitation signal, triggering projection acquisition of the CT machine at specific amplitude levels of the exciter amplitude, adjusting the period of the mechanical exciter by triggering from the CT, so that the acquired phases match, as well as simply allocating time stamps to each projection of the CT machine and allocating time stamps to different phases of the mechanical exciter signal, then selecting the projections that have the closest acquisition time to a specific phase of the exciter amplitude to be in the same projection group. This approach would be similar to what is referred to "retrospective gating" in cardiac CT, where the acquisition of projection data takes place in a normal manner, but the acquired slices are distributed to various phases of the periodic heart motion.

Using an extremely accurate periodic signal source for the mechanical exciter and the X-ray source power will lead to naturally synchronized acquisition of CT projections that are in phase with the mechanical exciter. Note that because the periodic excitation signal and the CT scanner projection angle trajectory are both controlled, both can be adjusted as a result of a "scout" scan that simply checks the synchronization between the CT angle and the mechanical exciter, without subjecting the patient to any radiation. For example, if a scan looks like as shown in FIG. 6., either the mechanical exciter signal period T and the time $T_S$ between the CT projection acquisition can be adjusted (T could be decreased and/or $T_S$ could be increased so that the ideal match (in FIG. 6 this means $4T_S=T$) between the two is achieved.

Thus, regardless of the synchronization process and the particular computing and hardware structure selected, the outcome of the CT data collection synchronized with the mechanical exciter is a data set 137 in which the total number $N_{CT}$ of projections per revolution is separated into $N_{phases}$ subsets $P_1, P_2, \ldots, P_{N_{phases}}$, or, more explicitly, $$P_1 = \{p(\theta(t_1 + T)), p(\theta(t_1 + 2T)), \ldots, p(\theta(t_1 + N_{views}T))\}; \quad (5)$$
$$P_2 = \{p(\theta(t_2 + T)), p(\theta(t_2 + 2T)), \ldots, p(\theta(t_2 + N_{views}T))\}$$
$$\vdots$$
$$P_{N_{phases}} = \{p(\theta(t_{N_{phases}} + T)),$$
$$p(\theta(t_{N_{phases}} + 2T)), \ldots, p(\theta(t_{N_{phases}} + N_{views}T))\}$$

These correspond to the exciter amplitude being at phases, $t=t_1+T$, $t=t_1+2T$, ..., followed by $t=t_2$, $t=t_2+T$, $t=t_2+2T$, ..., up to $t=t_{N_{phases}}$, $t=t_{N_{phases}}$, $t=t_{N_{phases}}+2T$, ..., etc., each of the subsets containing projection data of a tissue volume of interest 230 that is in the same state of deformation. While we have used the same number of views for each phase projection data for simplicity of exposition, it is clear that the number of views per phase is not necessary a constant $N_{views}$.

Variations of the synchronized CT acquisition with an external mechanical exciter will be obvious to those skilled in the art. For example, the single projections that correspond to each of the phases of the mechanical exciter period could be replaced with projection segments triggered at a given phase of the exciter, e.g. instead of the individual projections corresponding to the first row in (4), a set of projections $P_1=\{p(\theta([t_1+T,t_1+T+\Delta]), p(\theta([t_1+2T,t_1+2T+\Delta]), \ldots,\}$ could be acquired starting at $t=t_1+T$, through to time $t=t_1+T+\Delta$ for some small time increment $\Delta$. The projection angle sector that corresponds to this increment could be as long as the desired temporal resolution in sampling the phases of the periodic signal of the mechanical exciter.

The acquisition of projections that are synchronized with the periodic exciter has been discussed in detail above for planar acquisition. Extensions of the above to 3D acquisition are within the skill of a person the skilled in the art and is therefore not further describe herein. For multi-slice CT scanners, the same approach presented above holds for native volume acquisition. With discrete slice-by-slice table motion, the projection acquisition can be carried in the usual manner, with synchronization of projection timing resuming after each table step. The periodic excitation applied to the patient does not need to stop during the process of multi-slice acquisition. The projection angles acquired from one slice to the next do not have to be the same, as long the projection sets continue to be acquired in a manner synchronized with the exciter. For spiral CT acquisition, the interpolation of the projection data to a single slice plane must be carried out with projections that are in-phase. Preferably, in order to avoid a large interpolation gap, the pitch of the table should be such that there is an integer number of mechanical exciter periods for the same angle with respect to the CT axis 171 (FIG. 8). Let the helical CT pitch 170 be equal to d, and constant table velocity equal to v. Then, a preferable scanner table velocity is $v=d/N_{CT}T$, where there are $N_{CT}$ projections 111 acquired for one source rotation. For the example of FIGS. 2 and 3, $N_{CT}=48$.

Figure 9:
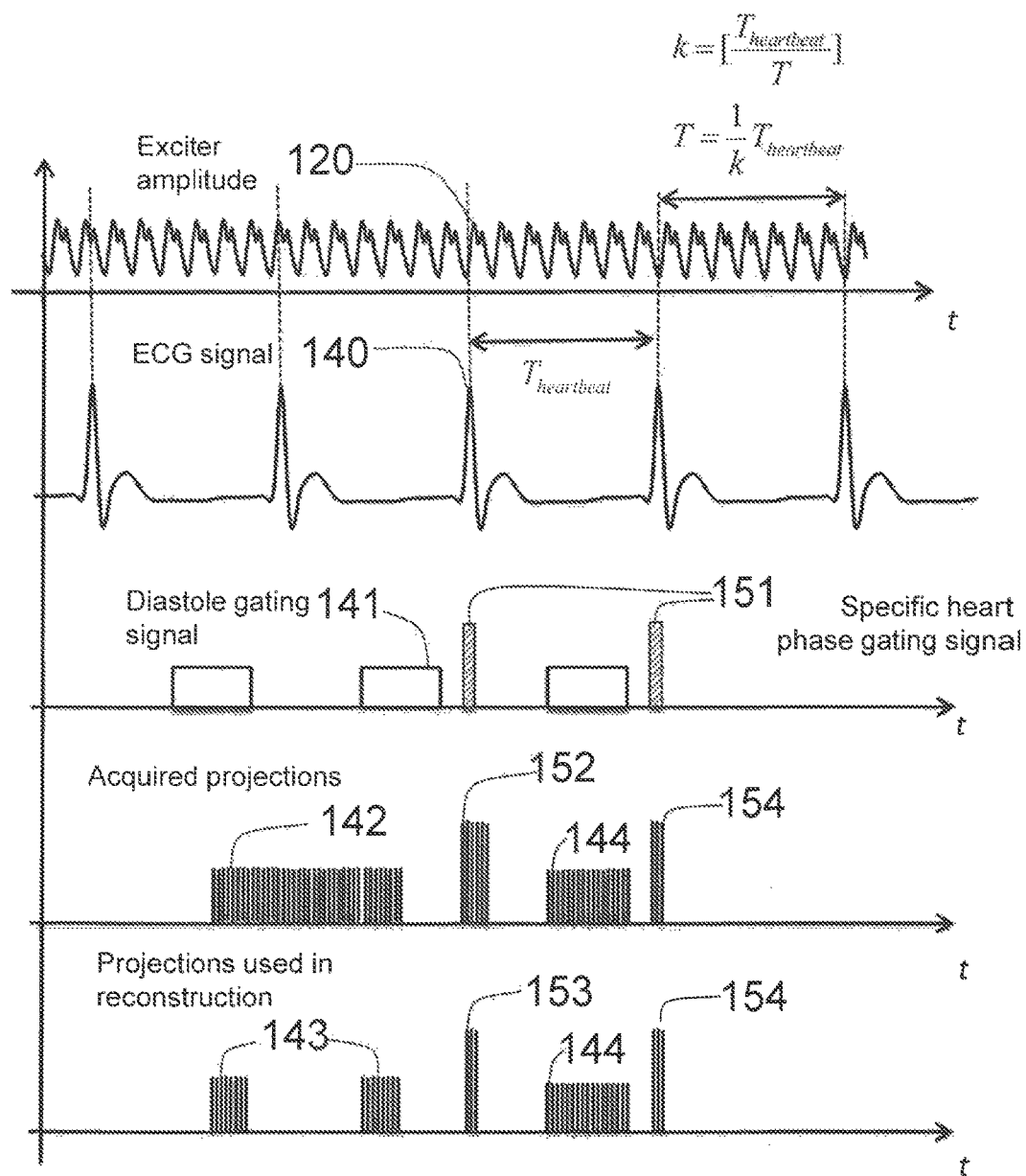
FIG. 9 is a graph illustrating an example gated acquisition of CT projections synchronized with an external periodic

Natural body motion caused by respiration and heart beating may interfere with the periodic tissue motion generated by the external exciter. Cardiac motion has typical frequency content that can reach 10 Hz. To deal with this significantly faster disturbance to the mechanical exciter, gating techniques from cardiac CT can be used. As explained in many articles on cardiac CT, as surveyed in, for example, in "Cardiac CT and MR for Adult Congenital Heart Disease", edited by F. Saremi, Springer, N Y, 2014, or in J.-F. Paul and H. C. Abada, "Strategies for reduction of radiation does in cardiac multislice CT", *Eur. Radiol.*, 2007, 17:2028-2037, which are incorporated herein by reference, the collection of CT projection data that is synchronized with the mechanical exciter can be gated based on the ECG. As illustrated in FIG. 9, in one approach, the ECG signal 140 is used to remove from the projection data those projections that are not acquired during a gating window 141. The gating window 141 could select a period from the diastole in which the heart is moving slowly. In retrospective gating, the projections 142 are acquired even when the gate signal is not on, and a number of projections are removed to select a gated set of projections 143 that are actually used in the reconstruction. Alternatively, a lower radiation level can be achieved by prospective gating in which the projection data 144 is only acquired during the gate window 141, i.e. only gated data that is used in the image reconstruction is actually acquired. With modern CT scanners, it is possible to obtain a full scan of a significant volume of interest, e.g. covering the full heart, within a single heartbeat, as illustrated in 144 of FIG. 9. This is achieved with multi-slice detectors (320 slices, for example, in a Toshiba™ CT), or with dual-source systems (2×128 slices, for example, in a Siemens™ CT). Alternatively, the acquisition of a full data set can be carried out in multiple segments over multiple heartbeats. The data set 143, acquired over two heartbeats, is equivalent to the data set 144, acquired during a single heartbeat. Narrow cardiac phase gating 150 can also be applied, prospectively (projections from the set 152 are eliminated to yield the set 153 actually used in the reconstruction) or retrospectively (154), in order to acquire a CT image during a specific heart phase. CT vendors have developed methods for automatic selection of best phases for cardiac image reconstruction and editing of ECG tracing and reconstruction windows in patients with irregular heart rates. These can be applied within the context of this invention with the only proviso that the acquired projections illustrated as 142, 144, 152 or 154, be synchronized to the mechanical exciter, even if the mechanical period T of the exciter is being adjusted as described below.

In order to keep the tissue motion as closely as possible to being periodic, the period of the mechanical exciter amplitude 120 can be adjusted so as to have an integer number of exciter periods within a heart beat. As illustrated in FIG. 9, the estimated heartbeat period from the ECG, $T_{heartbeat}$, is used to adjust the exciter period $$T = \frac{1}{k} T_{heartbeat},$$

where $$k = \left[\frac{T_{heartbeat}}{T}\right]$$

=the integer part (floor/ceiling function) of the ratio between the heart period and the mechanical exciter period.

Similar gating techniques may be utilized for synchronized projection acquisition with the mechanical exciter can be used with respiratory motion, or a combination of cardiac and respiratory motion. In a typical application of dynamic elastography, the frequency content of the mechanical exciter is much higher than the frequency content of breathing motion, and in many cases breath-hold gating techniques can be applied to reduce breathing effects on the CT reconstruction. See, for example, Keall P J, Mageras G S, Balter J M, Emery R S, Forster K M, Jiang S B, et al. The management of respiratory motion in radiation oncology report of AAPM Task Group 76. *Med Phys* 2006; 33:3874-900, which is incorporated herein by reference.

In FIG. 7, a gating source 160 that could be cardiac such as the ECG, from a pulmonary pacing system that allows patients to control their own respiration, or a ventilation system is shown. The gating source enables adjustment of the period of the mechanical exciter system as described above, or the prospective gating of the CT projection data acquisition.

Once each of the projection data sets have been obtained, the tissue image within the volume of interest 230 can be reconstructed at each phase of tissue deformation. One approach involves the use of sparse-view CT reconstruction techniques. These techniques, surveyed, for example, in H. Kudo et al. "Image reconstruction for sparse-view CT and interior-CT—introduction to compressed sensing and differentiated backprojection", *Quantitative Imaging in Medicine and Surgery*, 3(3), pages 147-161, allow for accurate reconstruction even when few projections are used. Indeed, for example, the technique from E. J. Candés, M. B. Wakin and S. P. Boyd, "Enhancing sparsity by reweighted $l_1$ Minimization", demonstrates a 10-projection reconstruction of the Shepp-Logan phantom that has negligible error. Hence, in one approach to reconstructing each of the phases of the tissue, each of the projection sets $P_i$ (see equation (5) above) is used to reconstruct a CT image $f(x)(t_i)$ in Hounsfield units, where x is the spatial pixel (for 2D reconstruction) or voxel (for 3D reconstruction) location, at times $t_i$ corresponding to different tissue deformation states.

This amounts to reconstructing $N_{phases}$ of tissue deformation states from the entire set of projection data (5), while the tissue is vibrated by the external exciter system 131, as opposed to reconstructing a single tissue phase from an equally rich data set. Because the tissue motion caused by the external mechanical exciter is very small, the entire data set (5) can be used to reconstruct a single average tissue image $\bar{f}(x)$ that is the average of the tissue phases $f(x)(t_i)$ as in conventional CT and is computed based on all the projections, with little noticeable difference relative to the image that would be obtained if the external exciter were off. However, there are significant differences between the average value $\bar{f}(x)$ and each of the individual phases that can be used to quantify tissue strain with sub pixel accuracy according to many techniques studied in the image processing and computer vision literature, as referenced, for example, in R. Szeliski, "Computer Vision: Algorithms and Applications", Springer 2012, http://szeliski.org/Book which is incorporated herein by reference.

In one approach the tissue phase $f(x)(t_k)$ at time instance $t_k$ is assumed to be caused by a deformation of $f(x+u_{ik}(x))(t_i)$ at time $t_i$. The deformation field $u_{ik}(x)$ between the two deformation states $f(x)(t_k)$ at time $t_k$ and $f(x+u_{ik}(x))(t_i)$ at time $t_i$, specifies a three-dimensional displacement vector at every voxel of $u_{ik}(x)$, and $f(x)(t_i)$ can be estimated by using a pattern matching function (e.g. 3D normalized cross-correlation over tissue patches as done in Zahiri R., Goksel, O. and Salcudean S. E. "Sub-sample displacement estimation from digitized ultrasound RF signals using multi-dimensional polynomial fitting of the cross-correlation function." Ultrasonics, Ferroelectrics and Frequency Control, IEEE Transactions on 57.11 (2010): 2403-2420.), which is incorporated herein by reference. Alternatively, salient features can be determined in the image $f(x)(t_k)$ at time instance $t_k$, and the deformation field $u_{ik}$ to time $t_i$ can be estimated based on the estimated displacement of these salient features and interpolated elsewhere in the image by using interpolation functions. Such features could be, for example, Modality independent neighbourhood descriptor (MIND) features as described in Heinrich, M. P., Jenkinson, M., Bhushan, M., Matin, T., Gleeson, F. V., Brady, S. M., & Schnabel, J. A. (2012). MIND: Modality independent neighbourhood descriptor for multi-modal deformable registration. *Medical Image Analysis*, 16(7), 1423-1435, which is incorporated herein by reference. Alternatively, there are many deformable registration techniques that find the deformation field $u_{ki}(x)$ between two images $f(x)(t_k)$ and $f(x)(t_i)$ that involve a cost function between the two images and a regularizing term that constraints the deformation field to one described by continuum mechanics, as explained, for example, in Modersitzki, Jan. "Numerical methods for image registration". OUP Oxford, 2003, which is incorporate herein by reference. The deformation constraints can impose equivoluminal deformation or deformation governed by a specific set of Lame parameters, including the shear modulus $\mu(x)$ in the volume of interest.

It should be noted that once the deformation fields between various tissue phases $f(x)(t_k)$ at time instance $t_k$ are obtained, the averaging or smearing effect that may be noticed in the average $\bar{f}(x)$ can be reduced by averaging not the tissue phases but rather by averaging the deformed tissue phases. Hence, at each tissue phase $t_k$, an improved image $\bar{f}(x)$ may be obtained by averaging all the tissue phases that are deformed back to a single state. For example, if $f(x)(t_i)=f(x+u_{ik}(x))(t_j)$, then $\frac{1}{2}[f(x)(t_k)+f(x-u_{ik}(x))(t_j)]$ is an improved image average over that obtained by adding up the two phases $\frac{1}{2}[f(x)(t_k)+f(x)(t_i)]$ without deformation.

As shown in Zahiri R., Goksel, O. and Salcudean S. E. "Sub-sample displacement estimation from digitized ultrasound RF signals using multi-dimensional polynomial fitting of the cross-correlation function." Ultrasonics, Ferroelectrics and Frequency Control, IEEE Transactions on 57.11 (2010): 2403-2420.) and in references therein all of which are incorporated by reference, the deformation $u_{ik}$ (x) between the tissue states $f(x)(t_k)$ and $f(x)(t_i)$ can be used to compute and display one-dimensional, two dimensional or three-dimensional strain images as known in the state of the art. Furthermore, $u_{ik}$ (x) can be viewed as a three-dimensional vector function of discrete time $\{u_{ik}(x)\}=\{u(x)(t_i-t_k)\}$ with respect to a reference $t_k$. Therefore, a transfer function and a coherence function between the source excitation $\{e(t_i-t_k)\}$ and the vector deformation function $\{u(x)(t_i-t_k)\}$, viewed as discrete periodic sequences, can be computed and used to characterize and display tissue, as taught, for example, in Salcudean, Septimiu E., et al. "Viscoelasticity modeling of the prostate region using vibro-elastography." Medical Image Computing and Computer-Assisted Intervention-MICCAI 2006. Springer Berlin Heidelberg, 2006. 389-396, which is incorporated herein by reference. Alternatively, the source excitation used in the computation of the transfer function and/or coherence can be replaced with a localized or averaged displacement.

The results of elastography imaging depend on the frequency of the mechanical excitation that is applied to deform the tissue. Static/quasi-static and dynamic elastography techniques have been reported. At low frequencies (quasi-static elastography), tissue excitation results in long spatial wavelengths. Computing elasticity parameters in such quasi-static conditions is challenging, even if the forces applied to the tissue and the boundary conditions are measured. Thus at low excitation frequencies, more information is derived from a display of deformation or strain than from the computation of intrinsic tissue properties. The display of strain may be useful for inferring what tissue volumes have abnormal elastic properties.

At low temporal frequency of the mechanical excitation (typically lower than 20 Hz), the inverse of tissue strain may provide an estimate of the relative tissue elasticity in a volume of interest. This is because softer tissue deforms more than stiffer tissue as a result of a mechanical compression. Therefore strain images can be used to infer tissue elasticity but not in a quantitative way, as the distribution of stress is not known throughout the volume of interest. In the 10-20 Hz range, in addition to strain, tissue relaxation time may also be measured as described in Eskandari, H., Salcudean, S. E., & Rohling, R. (2008), "Viscoelastic parameter estimation based on spectral analysis", *IEEE Transactions on Ultrasonics, Ferroelectrics and Frequency Control*, 55(7), 1611-1625, which is incorporated herein by reference. In addition to tissue strain, it has been shown that transfer function images which display the magnitude and phase of the transfer function from a reference (e.g. tissue exciter amplitude or an averaged tissue strain over a volume of interest) to a particular spatial location provides stable images that are useful for delineation of the prostate and for cancer localization—see for example, Moradi, M., et al. (2014). Multiparametric 3D in vivo ultrasound vibroelastography imaging of prostate cancer: Preliminary results. Medical physics, 41(7), 073505, and references therein, all of which are incorporated herein by reference.

At higher frequencies, tissue inertial forces become significant and, with the assumption of constant density, can be used in a tissue model to recover tissue elasticity or shear modulus from measured tissue displacements using quantitative elastography techniques, as described in Eskandari, H., Salcudean, S. E., Rohling, R., & Ohayon, J. (2008), "Viscoelastic characterization of soft tissue from dynamic finite element models", *Physics in medicine and biology*, 53(22), 6569, and also in U.S. Pat. No. 8,394,026, which are incorporated herein by reference. Shear modulus is solved with higher resolution and accuracy when the spatial wavelength of the deformation wave generated in tissue is small, or when the temporal frequency of excitation is high. However, the higher frequency waves in tissue are more rapidly attenuated so they are more difficult to transmit into a particular organ.

The mechanical waves induced into tissue by external exciters in most of the previous mentioned techniques vary in both space and time. An ideal measurement system would measure all three components (x,y,z) of the displacements instantaneously over a volume or region of interest. 3D vector fields of 3D displacements as a function of time would provide a mathematically complete representation of the wave propagation. However, such ideal measurements systems are currently infeasible, so most previously mentioned methods employ a harmonic (sinusoidal) excitation and they exploit the steady state nature of the wave propagation to build its complete representation through multiple measurements of the tissue state.

In MRE, this is achieved usually by synchronizing the image acquisition with the mechanical exciter that is creating the waves and using a harmonic excitation.

Based on the known tissue deformation field $u_{ik}$ (x), a number of methods have been developed in the context of ultrasound and MRI elastography to determine the tissue shear modulus at a number of frequencies. We note that the deformation field field $u_{ik}$(x), i=1, 2, ... $N_{phases}$ is a periodic discrete 3D sequence. In one approach, 3D displacement phasors U(x, jω) are obtained from this sequence by taking its Fourier series, its Discrete Fourier Transform, or by a data fit to the selected frequencies $\omega_i$ applied by the mechanical exciter—see, for example, Honarvar, M., Salcudean, S. E., & Rohling, R. (2014, March). Vibro-elastography: direct FEM inversion of the shear wave equation without the local homogeneity assumption. In SPIE Medical Imaging (pp. 904003-904003) International Society for Optics and Photonics, and Honarvar, M., Sahebjavaher, R., Sinkus, R., Rohling, R., & Salcudean, S. (2013). Curl-based Finite Element Reconstruction of the Shear Modulus Without Assuming Local Homogeneity: Time Harmonic Case, and Eskandari, H., Salcudean, S. E., Rohling, R., & Ohayon, J. (2008). Viscoelastic characterization of soft tissue from dynamic finite element models. Physics in medicine and biology, 53(22), 6569, and Baghani, A., Eskandari, H., Rohling, R. N., & Salcudean, S. E. (2014), and U.S. Patent Application Publication No. 2014/0330122, all of which are incorporated herein by reference.

In these approaches, at one or several selected frequencies co of the Fourier series of the mechanical exciter signal 120, the model of tissue deformation in the volume of interest is described by a mass-spring-damper differential equation:

$$\omega^2 M(x)U(x,j\omega)+j\omega B(x)U(x,j\omega)+K(x)U(x,j\omega)=0,$$

written here for convenience in the frequency domain, where U(x,jω) is a vector of 3D displacement phasors for the volume of interest, and the matrices M(x), B(x), K(x) are obtained by various finite element techniques and depend on the distribution of complex shear modulus μ(x) in the volume of interest, as described in [Eskandari et al, 2008], incorporated by reference in this description. Typically, M(x) is a diagonal mass matrix that assumes a constant tissue density M. Furthermore, the shear modulus is solved from a linear system of equations as described in [Honarvar M. et al, 2013], incorporated by reference in this description. This linear system of equations has the form $A(U(x,j\omega))\mu(x)=b(\omega,\rho(x), U(x, j\omega))$, where the matrix $A(U(x,j\omega))$ and the column vector $b(\omega, \rho(x), U(x,j\omega))$ depend on the deformation phasor $U(x,j\omega)$, on frequency and on the tissue density. This system is typically overdetermined, and one typically assumes that the tissue density $\rho(x)=\rho$, is a constant=1000 kg/m³. At multiple frequencies, multiple systems of equations can be stacked up to determine a single shear modulus distribution consistent with data from multiple frequencies. Alternatively, the shear modulus can be modelled as a frequency dependent quantity $\mu(x)(\omega)$ and the parameters of the model can be found.

Because at typical energies used in the X-ray beams, the CT image is mostly determined by tissue density and varies linearly with it, without additional imaging, the average CT image $\bar{f}(x)$ provides a more accurate density map $\rho(x)$ that can be substituted in the linear equations that is used for the complex shear modulus distribution in the volume of interest, $A(U(x,j\omega))\mu(x)=b(\omega,\rho(x), U(x,j\omega))$.

Thus, in one elasticity reconstruction process as described above, the following steps are used to obtain a quantitative elasticity map: First, each of the tissue phase images $f(x)(t_i)$, from each of the $N_{phases}$ projection sets $P_1, P_2, \ldots P_{N_{phases}}$, are obtained. Second, the deformation fields $\{u_{ik}(x)\}=\{u(x)(t_i-t_k)\}$ between the different tissue phase images are obtained with respect to a reference tissue phase image $f(x)(t_k)$, at time $t_k$. Third, the shear modulus $\mu(x)$ is obtained from a model of the tissue deformation between phases which can be derived from finite-element or other continuum mechanics techniques, and the values of the tissue deformation fields $\{u(x)(t_i-t_k)\}$. In one elasticity reconstruction process, the model can be expressed as a mass-spring-damper matrix model $$M(x)\frac{d^2}{dt^2}u(x)(t_i-t_k) + B(x)\frac{d}{dt}u(x)(t_i-t_k) + K(x)u(x)(t_i-t_k) = 0$$

with frequency domain representation $-\omega^2 M(x)U(x,j\omega)+j\omega B(x)U(x,\omega)+K(x)U(x,\omega)=0$, where $U(x,\omega)$ is a phasor representation of $\{u(x)(t_i-t_k)\}$. This frequency representation is linear in parameters, and can be written as $A(U(x, j\omega))\mu(x)=b(\mu(x),\rho(x), U(x,j\omega))$ from which the tissue shear modulus $\mu(x)$ distribution is obtained at one or several frequencies $\omega$ of the phasors $U(x,j\omega)$ of $\{u(x)(t_i-t_k)\}$, i=1, 2, ..., $N_{phases}$.

In an alternative approach, the tissue phase images $f(x)(t_k)$, the tissue deformation fields $\{u(x)(t_i-t_k)\}$ and the tissue shear modulus $\mu(x)$ are obtained by solving a large system of simultaneous equations. These equations comprise:
(i) $N_{phases}$ sets of projection equations, corresponding to the tissue being in the different phases of the periodic motion, as described in the following equation (6):

$$P_1 = Proj\{f(x)(t_1)\}$$
$$P_2 = Proj\{f(x)(t_2)\} = Proj\{f(x+u(x)(t_2-t_1))(t_2)\}$$
$$\ldots$$
$$P_{N_{phases}} = Proj\{f(x)(t_{N_{phases}})\} = Proj\{f(x+u(x)(t_{N_{phases}}-t_1))(t_{N_{phases}})\}$$

and, (ii) a set of equations corresponding to the dynamic model of tissue:

$$A(U(x,j\omega))\mu(x)=b(\omega,\rho(x),U(x,j\omega)),$$

where $U(x,j\omega)$ is a phasor of $\{^{11}(x)(t_i-t_k)\}$, i=1, 2, ..., $N_{phases}$ at one or several of the spectral lines $\omega$.

In the two-dimensional case, each of the sets of projections $P_i=Proj\{f(x)(t_i)\}$, i=1, ... $N_{phases}$ comprises $N_{views}$ projections of tissue that is in the same state of deformation as the tissue $f(x+u(x)(t_i-t_1))(t_i)\}$ at time $t_i$, as described in (5), and each projection $P_i=\{p(\theta(t+T)), p(\theta(t_i+2T)), \ldots, p(\theta(t+N_{views}T))\}$, has as many distinct equations $$p(\theta(t_i+lT))(\varphi) = \int f\left(r\begin{bmatrix}\cos\theta(t_i+lT)\\\sin\theta(t_i+lT)\end{bmatrix}+s\begin{bmatrix}\cos(\theta(t_i+lT)+\varphi)\\\sin(\theta(t_i+lT)+\varphi)\end{bmatrix}+u\right)ds$$

as there are detector elements or distinct angles $N_{detectors}$ in $[-\varphi_{max},\varphi_{max}]$ (see FIG. 1a and FIG. 1.b, (20a-21a), (20b-21b), ..., (20g-21g)). In the above, the line integral corresponds to the attenuated X-ray detected at the detector at angle cp relative to the detector source which is at angle θ.

In this alternative approach, a very large number of equations are solved, with unknowns being one Hounsfield number, three deformation values, and one complex shear modulus value, at every voxel in the volume of interest 230. Regularization techniques that include minimization of the total variation of $\mu(x)$ and/or of $u(x)(t_i-t_1)$ (e.g., E. J. Candés, M. B. Wakin and S. P. Boyd, "Enhancing sparsity by reweighted $l_1$ Minimization") or sparsity regularization through the discrete cosine transform (e.g., Honarvar, M., R. S. Sahebjavaher, S. E. Salcudean, and R. Rohling. "Sparsity regularization in dynamic elastography." *Physics in medicine and biology* 57, no. 19 (2012): 5909, which is incorporated herein by reference) may be employed for more effective solutions.

In the above description, the periodic excitation can be a sinusoid, a sum of sinusoids, a sawtooth wave, a square wave etc. The extent of the number of samples/phases/tissue states depends on the signal to ratio of the image, and the level of "texture" detail that is obtained in CT. This level of detail is given, to the first order, by changes in tissue density. Based on this, it is likely that a good application of this dynamic elastography invention is in the imaging of lung nodules. However, it might be possible to image the heart with a periodic excitation that exceeds the heartbeat with the same techniques, as well as the liver, the brain and different muscles.

When it is difficult to generate significant motion in an internal organ at high enough frequency to reconstruct of an absolute elasticity map, a low-frequency strain image at up to 20 Hz may provide a good estimate of relative elasticity.

The above description CTE also applies to fifth generation stationary scanners in which the source does not rotate. The principle of synchronization between the mechanical exciter and the CT projection acquisition remains the same, with further flexibility gained from not having to worry about the CT gantry rotation.

The invention claimed is:
1. A method of performing elastography of a volume of tissue of a patient with a CT scanner, comprising:
applying, by a vibration source, a periodic excitation wave to the volume of tissue, the periodic excitation wave having a plurality of phases that each correspond to a respective one of a plurality of deformation states of the volume of tissue;

acquiring by the CT scanner a first plurality of CT projections at a first phase corresponding to a first deformation state of the volume of tissue, the first plurality of CT projections comprising a first CT projection set;

acquiring by the CT scanner a second plurality of CT projections at a second phase corresponding to a second deformation state of the volume of tissue, wherein the second phase is different than the first phase, the second plurality of CT projections comprising a second CT projection set;

determining, based on the first CT projection set and the second CT projection set, at least one of a tissue deformation field and a tissue mechanical property of the volume of tissue.

2. The method according to claim 1, wherein acquiring the first plurality of CT projections and the second plurality of CT projections comprise selecting at least one of an excitation wave period (T) of the vibration source and a CT scanner projection acquisition period ($T_S$) that satisfy $lT=kT_S$, where l and k are integers.

3. The method according to claim 1, wherein acquiring at least one of the first plurality of CT projections and the second plurality of CT projections further comprises removing CT projections from the at least one of the first plurality of CT projections and the second plurality of CT projections acquired outside of a gate window.

4. The method according to claim 3, further comprising selecting an excitation wave period such that a heartbeat period of the patient is an integer number of the excitation wave period.

5. The method according to claim 3, further comprising determining the gate window based on at least one of an electro cardio gram (ECG) signal and a respiration rate of the patient.

6. The method according to claim 1, wherein the determining comprises determining a deformation field based on the first CT projection set and the second CT projection set.

7. The method according to claim 6, wherein the determining comprises determining a shear modulus of the volume of tissue based on the deformation field.

8. The method according to claim 7, wherein the determining comprises determining a change in the shear modulus as a function of frequency of the periodic excitation waves applied by the vibration source.

9. The method according to claim 6, wherein the determining comprises determining coherence between the periodic excitation waves and the determined deformation field.

10. A system for performing elastography of a volume of tissue of a patient, the system comprising:

a computed tomography (CT) scanner having an X-ray source and detectors for generating CT projections of the volume of tissue;

a vibration source for generating a periodic excitation wave;

a processor coupled to the CT scanner and the vibration source, the processor configured to:

apply, by the vibration source, the periodic excitation wave to the volume of tissue, the periodic excitation wave having a plurality of phases that each correspond to a respective one of a plurality of deformation states of the volume of tissue;

acquire, by the CT scanner, a first plurality of CT projections at a first phase corresponding to a first deformation state of the volume of tissue, the first plurality of CT projections comprising a first CT projection set;

acquire, by the CT scanner, a second plurality of CT projections at a second phase corresponding to a second deformation state of the volume of tissue, wherein the second phase is different than the first phase, the second plurality of CT projections comprising a second CT projection set;

determine, based on the first CT projection set and the second CT projection set, at least one of a tissue deformation field and a tissue mechanical property of the volume of tissue.

11. The system according to claim 10, wherein the processor is further configured to acquire the first plurality of CT projections and the second plurality of CT projections comprise selecting at least one of an excitation wave period (T) of the vibration source and a CT scanner projection acquisition period ($T_S$) that satisfy $lT=kT_S$, where l and k are integers.

12. The system according to claim 10, wherein the processor is further configured to acquire at least one of the first plurality of CT projections and the second plurality of CT projections further comprises removing CT projections from the at least one of the first plurality of CT projections and the second plurality of CT projections acquired outside of a gate window.

13. The system according to claim 12, wherein the processor is further configured to select an excitation wave period such that a heartbeat period of the patient is an integer number of the excitation wave period.

14. The system according to claim 12, wherein the processor is further configured to determine the gate window based on at least one of an electro cardio gram (ECG) signal and a respiration rate of the patient.

15. The system according to claim 10, wherein the processor is further configured to determine a deformation field based on the first CT projection set and the second CT projection set.

16. The system according to claim 15, wherein the processor is further configured to determine a shear modulus of the volume of tissue based on the deformation field.

17. The system according to claim 16, wherein the processor is further configured to determine a change in the shear modulus as a function of frequency of the periodic excitation waves applied by the vibration source.

18. The system according to claim 15, wherein the processor is further configured to determine coherence between the periodic excitation waves and the determined deformation field.

19. A method of concurrently obtaining a CT image and a tissue deformation field of a volume of tissue undergoing a deformation, comprising:

acquiring, by a CT scanner, at least a first CT projection set corresponding to a first deformation state of the volume of tissue;

deforming the volume of tissue to generate a second deformation state in the volume of tissue;

acquiring a second CT projection set corresponding to the second deformation state of the volume of tissue;

reconstructing a first CT image of the volume of tissue based on the first CT projection set, and a second CT image based on the second CT projection set;

determining the tissue deformation field based on the first CT image and the second CT image;

generating a modified second CT image by removing tissue deformation from the second CT image based on the tissue deformation field; and averaging the first CT image and the modified second CT image to generate an improved CT image.

* * * * *